United States Patent [19]

Chang et al.

[11] Patent Number: 5,010,003

[45] Date of Patent: Apr. 23, 1991

[54] USE OF YEAST HOMOLOGOUS SIGNALS TO SECRETE HETEROLOGOUS PROTEINS

[75] Inventors: Chung N. Chang, San Mateo; Ronald A. Hitzeman, Pacifica; Mark D. Matteucci, San Francisco, all of Calif.

[73] Assignee: Genentech, Inc., South San Francisco, Calif.

[21] Appl. No.: 541,186

[22] Filed: Jun. 20, 1990

Related U.S. Application Data

[63] Continuation of Ser. No. 488,387, Apr. 25, 1983, abandoned.

[51] Int. Cl.$^5$ ............... C12P 21/00; C12P 21/02; C12N 15/00
[52] U.S. Cl. .................... 435/69.9; 435/69.5; 435/69.51; 435/172.3; 435/320; 435/255; 435/256; 435/69.1; 435/69.8; 536/27; 935/37; 935/47; 935/48
[58] Field of Search ............ 435/69.1, 69.5, 69.51, 435/172.3, 255, 256, 320; 536/27; 935/37, 47, 48

[56] References Cited

U.S. PATENT DOCUMENTS 4,338,397 7/1982 Gilbert et al. .................. 435/68
4,546,082 10/1985 Kurjan et al. .................. 435/172.3

OTHER PUBLICATIONS

Thomer from "The Molecular Biology of the Yeast Succharomyces", Strathern et al., Editors, pp. 161-163, 1981.
Carlson et al., Cell, vol. 28, pp. 145-154, 1982, "Two Differentially Regulated mRNAs with Different 5' End & Encode Secreted and Intracellular Forms of Yeast Intervase."
Hitzeman et al., Science, vol. 219, Feb. 11, 1983, pp. 620-625, "Secretion of Human Interferons by Yeast".
Talmadge et al., Nature, vol. 294, p. 176, 1981.
Tuite et al., EMBO Journal, vol. 1(5), pp. 603-608, 1982, "Regulated High Efficiency Expression of Human Interferon-Alpha in Succharoinyces".
Hitzeman et al., J. Biol. Chem., vol. 255(24), 12-25-80, pp. 12073-12080, "Isolation and Characterization of the Yeast 3-phosphoglycerokinase Gene (PGK), by an Immun. Screening Technique".
Hitzeman et al., Nature, vol. 293, (5835), pp. 717-722, Oct. 29, 1981, "Expression of a Human Gene for Interfoning Yeast".
Davis et al., Nature, vol. 2836, pp. Jan. 31, 1980, "The Mechanism of Protein Secretion across Membranes".
Silhavy et al., Micro. Rev., Sep. 1983, vol. 47(3), pp. 313-344, "Mechanisms of Protein Localization".
Talmadge et al., Proc. Natl. Acad. Sci., vol. 77(6), Jun. 1980, pp. 3369-3373, "Eukaryotic Signal Sequence Transports Insulin Antigen in E. coli".
Kadonaga et al., J. Biol. Chem., vol. 259(4), Feb. 25, 1984, pp. 2149-2154, "The Role of the β-lactamase Signal Sequence in the Secrection of Proteins by E. coli".
Bassford et al., J. Bact., vol. 137(1), Jul. 1979, pp. 19-31, "Use of Gene Fusion to Study Secretion of Maltose-Binding Protein into E. coli Periplasm".
Kurjan, J. et al., "Cell", 30:933-943, (Oct. 1982).
Perlman, D. et al., "Proc. Natl. Acad. Sci. U.S.A.", 79:781-785, (Feb. 1982).

Primary Examiner—Robin L. Teskin
Attorney, Agent, or Firm—Janet E. Hasak

[57] ABSTRACT

Described herein is the secretion from yeast of heterologous protein via a preprotein in which the heterologous protein is fused to the signal peptide of a yeast protein. The preprotein is processed by the cells to produce and secrete mature heterologous protein.

11 Claims, 19 Drawing Sheets

Fig.2.

```
                                  5                    10                   15         20
                            MetLeuLeuGluAlaPheLeuPheLeuLeuAlaGlyPheAlaAlaLysIleSerAlaSerMetThrAsnGlu
1. Preinvertase             ATGATGCTTTGCAAGCTTTCCTTTCCTTTTGGCTGGTTTGCAGCCAAAATATCTGCATCAATGACAAACGAA MetLeuLeuGluAlaPheLeuPheLeuLeuAlaGlyPheAlaAlaLysIleSerAlaMetCysAspLeuPro
2. Invertase signal -
   LeIFA                    ATGATGCTTTGCAAGCTTTCCTTTCCTTTTGGCTGGTTTGCAGCCAAAATATCTGCAATGTGTGATCTGCCT MetLeuLeuGluAlaPheLeuPheLeuLeuAlaGlyPheAlaAlaLysIleSerAlaMetCysAspLeuProGln
3. Invertase signal -
   LeIFA (F2)               ATGATGCTTTGCAAGCTTTCCTTTCCTTTTGGCTGGTTTGCAGCCAAAATATCTGCAATGTGTGATCTGCCTCAA MetLeuLeuGluAlaPheLeuPheLeuLeuAlaGlyPheAlaAlaLysIleSerAlaAlaCysAspLeuProGln
4. Invertase signal -
   LeIFA (E3)               ATGATGCTTTGCAAGCTTTTCCTTTTCCTTTTGGCTGGTGGTTTGCAGCCAAAATATCTGCATGTGATCTGCCTCAA
```

Fig. 13. PART A.

```
CTGATATACCGAAAAATGCATAAATATCTCTCTAGTTTGTGCCTTTCTGTCGCCCTACCTCACAAAGAGAAGTACTGATGGCTAATAATTGTTGGATCGATATTGTTGGATCATTGTATCTCTT
AATGTCAACAGAGCATAAGTCAGACTCTTTGCCACTCTTTAAAAAGCTGCGAAGGCGAACGTGACTACGGGGTGCGAAGTTTGATGCTAATGACAGTTATCCAATGTT
TTGTTGTGTTCATTCAAACTATTTGAGCCTCACTGTTCATTTGTTTGACTACTAACATGGCAGCATGCCTCGTTCTAGGCTGCTAGCCAGGCTGTGAGAACCGTAAAATTAGCCTATGT
TCAACATTCTCTGCTTTCAATGTCACTGTTCATTTGTTACTATGAAAGTAGTTCGTCGCAATTTGTCTGCGACAGTCTTCTTTTGCAGTCAGATGAAGTGTCTTCTGAGAAA
TTGATGCTTTCAAATGGCCTTAAAAATTTTTGTATCATAGCTAACAACACATACTGTTGCGCCAGGGAAGTGAAATCATGGTTGTATATTACAATACATATGTGCATTACCAAGTA
TGGAAAAGCGGAAAGTCTGAAGAAGTTATGAAAAAGCCGAAAATAAAAAAAGTTATTTCCTGTGACTTCTCGGGAAGCAGTTAGACCTCCTTCGCTGTATTCTTAGGTGCT
ATACCTCATTTCCACGATGGTAATAGACGATCAGTCTATTAATGCGCTAAGAACGTAGAAAAGTTATTAACTGAAGAGCTTTGCTAATGCCGTCGCACATTAAACCGCTAGACATTG
CCTTGAATAGGAAGCCAATAATCTACGAATATCATGAGCTTCAGGGCCCTGCATATACTATAGTAAAAAAAACTAAGTTTCCCCTGTAGTAACAGGGAGATACCGTACGGAG
GTCTGAATTCCCTACAGAAGTAGCTGTAAAATTCAGAATTCGCAACAACCTATAATTGAGTTAAGTGCCTTCCAAGCTAAAAAGTTTGAGGTTATAGGGCTTAGCATCCACACGTC
ACAATCTCGGGTATCGAGTATGTAGTATGTAGAATTACGGCCAGGAGGTTTCCAATGAACAAGGACAGGGCACGGTTGAGCTGTCGAAGGTATCATTTATCATGTTTCGTTTGTACAA
GCACGACATACTAAGACATTACCGTATGGGAGTTGTCCTAGCGTAGTTCTCGCTCCAAAAGCTCAAAAAGTACGTCATTAGAATAGTTGTGAGCAAATTACCAGTCG
GTATGCTACGTTAGAAGGCCCACAGTATTCTTCTACCAAAGGGGTGCCTTTGTTGAACTCGATCCATTATGAGGGCTTCCATTATTCCCCGATTTTTATTACTCTGAACACGAATAA
AAGAAAAAAACCCAGTTTAGGAAATTATCCCGGGGCCGAAGAAATAACCCGTAGCGTTAATCGACCCCCAGTCCAGGGTTTTCCATGAGGTTTCTGAAAACTGACGAGGAATGTGAT
TATAAATCCCTTATGTGATGTCTAAGACTTTTAAGGTAACGGCCCGATGTTTGCCTATTACCATCATAGAGACGTTTCTTTTCGAGGAATGCTTAAACGACTTGTTGACAAAAATGTT
GCCTAAGGGCCTCTATAGTAAACCATTTGAAGAAAGATTTGACGACTTTTTTTTTTGGATTTCGATTCCATCCTATAATCCTTCCTCCTGAAAAGAACATATAAATAGATATGTATTATTCT
```

Fig. 13. PART B.

```
TCAAAACATTCTCTTGTCTTGTGCTTTTTTTTACCATATATCTTACTTTTTTTCTCAGAGAAACAAGCAAACAAAAGCTTTTCTTTTCACTAACGTATATG
                                                                                                      1
                                                                                                      met leu
                                                                                                      ATG CTT leu gln ala phe leu phe ala ala gly phe ala ala lys ile ala ser met thr asn glu thr ser asp arg pro leu val his
    TTG CAA GCT TTC CTT TTC GCT GCT GGT TTT GCA GCC AAA ATA TCA GCA ATG ACA AAC GAA ACT AGC GAT AGA CCT TTG GTC CAC
                  10                         20                         30                         60 phe thr pro asn lys gly trp met asn asp pro asn gly leu phe trp gly his ala lys trp his leu tyr phe gln tyr asn
    TTC ACA CCC AAC AAG GGC TGG ATG AAT GAC CCA AAT GGG TTG TTT TGG GGT CAT GCA AAA TGG CAT CTG TAC TTT CAA TAC AAC
                  40                         50                                                    60 pro asn asp thr val trp gly his thr ala ser met val val asp tyr asn asn thr pro glu asp leu thr ile ala ile
    CCA AAT GAC ACC GTA TGG GGT CAT ACT GCT TCC ATG GTG GTT GAT TAC AAC AAC ACG CCT GAA GAT CAA CCC ATT GCT ATC
                  70                         80                        110                        120 ala pro lys arg asn asp ser gly phe ser met thr pro glu ser gln phe trp tyr glu pro ser gln lys
    GCT CCC AAG CGT AAC GAT TCA GGC TTC TCT ATG ACT CCT GAA AGT CAA TTC TGG TAT GAA CCT TCT CAA AAA
                  100                        110                        180                        210 pro arg gln arg cys val ala ile trp thr tyr asn thr tyr ile ser gln tyr ile ser trp ser lys val phe trp lys ser trp leu lys ser ala phe
    CCA AGA CAA AGA TGC GTT GCG ATT TGG ACT TAC AAT AAC TCC ATT AGC TAT TCT GAT GGT TAC ACT
                  130                        140                        150 phe thr glu tyr gln lys pro val leu ala ala asn ser thr gln phe arg asp pro thr lys val phe trp tyr glu pro ser gln lys
    TTT ACT GAA TAC CAA AAG CCT GTT TTA GCT GCC AAC TCC ACT CAA TTC AGA GAT CCA CCT TAT GAA CCT TCT CAA AAA
                  160                        170                        180 trp ile met thr ala ala lys ile lys ile glu tyr ser ser trp ser lys val phe trp lys ser trp leu glu lys ser trp leu lys ser ala phe
    TGG ATT ATG ACG GCT GCC AAA ATT GAA TAC AGC TCT TGG TCC AAG CTA GAA TCT GCA TTT
                  190                        200                        210 ala asn glu gly phe leu val pro thr glu cys pro gln asp pro ser lys ser tyr trp val
    GCC AAT GAA GGT TTC CTT GTC CCA ACT GAG TGT CCA CAA GAT CCT TCC AAA TCT TAT TGG GTC
                  220                        230                        240 met phe ile ser ile asn pro ala gly gly ser phe val gly tyr phe asn gln his thr gly thr his phe glu ala
    ATG TTT ATT TCT ATC AAC CCA GCA GGT GGC TCC TTC GTT GGA TAT TTT AAT CAA CAT CAT ACT GGT ACT CAT TTT GAA GCG
                  250                        260                        270
```

Fig. 13. PART C.

```
                                                                               300
phe asp asn gln ser arg val val asp phe gly lys asp tyr tyr ala leu gln thr phe phe asn thr asp pro thr tyr gly ser ala
TTT GAC AAT CAA TCT AGA GTG GTA GAT TTT GGT AAG GAC TAC TAT GCC TTG CAA ACT TTC TTC AAC ACT GAC CCA ACC TAC GGT TCA GCA
                                                                               330
leu gly ile ala trp ala ser asn trp glu tyr ser ala phe val pro thr asn pro trp arg ser ser met ser leu val arg lys phe
TTA GGT ATT GCC TGG GCT TCA AAC TGG GAG TAC AGT GCT TTT GTC CCA ACT AAC CCA TGG AGA TCA TCC ATG TCT TTG GTC CGC AAG TTT
                                                                               360
ser leu asn thr glu tyr gln ala asn pro glu leu lys ala pro ile leu asn ile ser asn ile ser asn ala gly pro
TCT TTG AAC ACT GAA TAT CAA GCT AAT CCA GAG CTT AAA GCC CCA ATA TTG AAC ATT AGT AAT GCT GGT CCC
                                                                               390
trp ser arg phe ala thr asn thr leu thr lys ala asn ser tyr asn val asp leu ser asn ser thr leu gly thr leu glu phe glu
TGG TCT CGT TTT GCT ACT AAC ACA CTA ACT AAG GCC AAT TCT TAC AAT GTC GAT TTG AGC AAC TCG ACT GGT ACC CTA GAG TTT GAG
                                                                               420
leu val tyr ala val asn thr ile ser gln thr gln thr ile ser lys ser leu trp phe lys gly leu glu asp pro glu
TTG GTT TAC GCT GTT AAC ACC ATA TCC CAA ACC ATA TCC AAA TCC CTT TGG TTC AAG GGT TTA GAA GAT CCT GAA
                                                                               450
glu tyr leu arg met gly phe glu val ser ala ser ser phe leu asp leu arg gly asn ser lys val lys phe val lys glu asn pro
GAA TAT TTG AGA ATG GGT TTT GAA GTC AGT GCT TCT TCC TTC TTT TTG GAC CTT AGA GGT AAT TCT AAG GTC AAG TTT GTC AAG GAG AAC CCA
                                                                               480
tyr phe thr asn arg met ser val asn asn gln pro phe lys ser glu asn asp leu ser tyr tyr lys val tyr gly leu leu asp gln
TAT TTC ACA AAC AGA ATG TCT GTC AAC AAC CAA CCA TTC AAG TCT GAG AAC GAC CTA AGT TAC TAT AAA GTG TAC GGC CTA CTG GAT CAA
                                                                               510
asn ile leu glu leu tyr phe asn asp gly val val ser val val ser thr asn thr tyr phe met thr thr gly leu asn ala leu gly ser val asn
AAC ATC TTG GAA TTG TAC TTC AAC GAT GGA GTT GTC TCT GTT GTC AGT ACA AAT ACC TAC TTC ATG ACC ACC GGT AAC GCT CTA GGA TCT GTG AAC
                                    532
met thr gly val asp asn leu phe tyr ile asp lys phe gln val arg glu val lys AM
ATG ACC ACT GGT GTC GAT AAT TTG TTC TAC ATT GAC AAG TTC CAA GTA AGG GAA GTA AAA TAG AGGTTATAAAACTTATTGTCTTTTTATTTTTCA AAGCCATTCTAAAGGGCTTAGCTAACGAGTGACGAATGTAAAACTTTATGATTTCAAAGAATACCTCCAAACCATTGAAAATGTATTTTATTTTCCCGACCCCAGTTAC
CTGGAATTTGTTCTTTATGTACTTTATATAAGTATATAATTTCTTAAAAATTTTTACTACTTTGCAATAGACATCATTTTTCACGTAATAAACCCACAATCGTAATGTAGTTGCCTTACA
CTACTAGGATGGACCTTTTTGCCTTTATCTGTTTTGTTACTGACAAATGAAACACAATTAGTAGTTATGTGAAAATTTAAAAGCATTAAGTAGAAGTATACCATATATTGTAAAAAA
AAAAAGCGTTGTCTTCTACGTAAAAGTGTTCTCAAAAAGTAGTGAGGGAAATGATACCAAGCTATCTGTAACAGGAGCTAAAAAATCTCAGGGAAAAGC
```

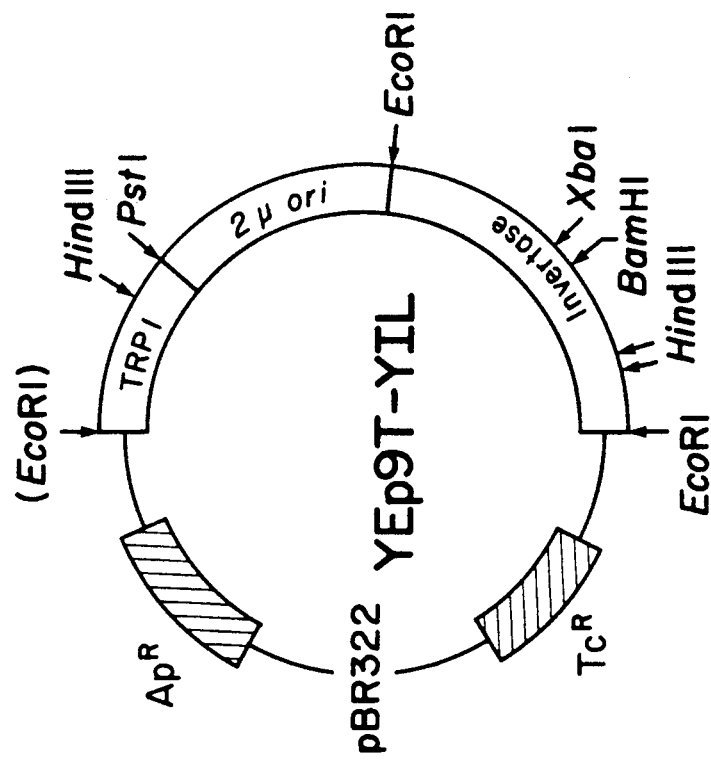
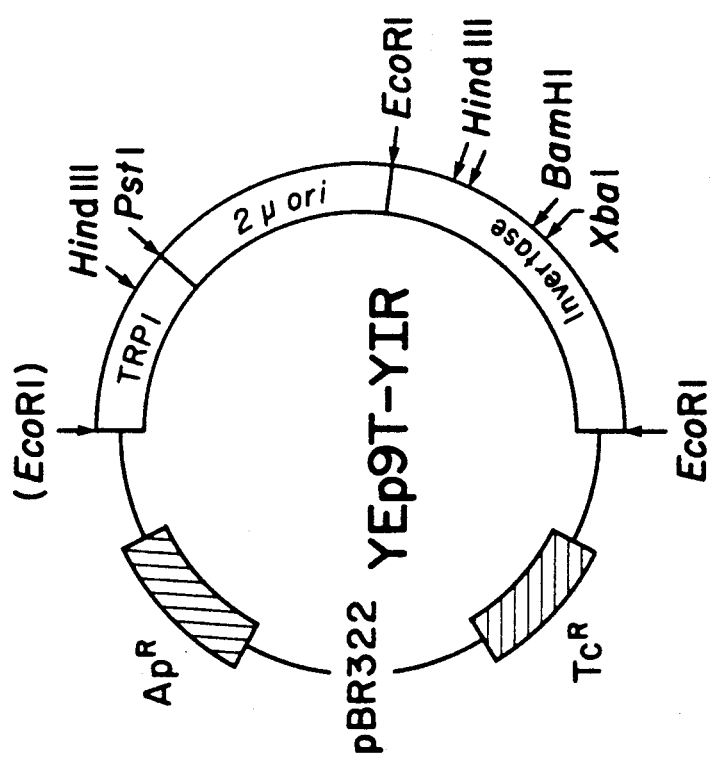
Fig.14.

USE OF YEAST HOMOLOGOUS SIGNALS TO SECRETE HETEROLOGOUS PROTEINS

This is a continuation of co-pending application Ser. No. 488,337 filed on Apr. 25, 1983.

CROSS REFERENCE TO RELATED APPLICATIONS

This application is related to commonly assigned application Ser. No. 438,236 now U.S. Pat. No. 4,775,622 filed Nov. 1, 1982, and Ser. No. 488,323, now abandoned filed on even date herewith, the disclosures of which are hereby incorporated by reference.

FIELD OF THE INVENTION

This invention is directed generally to recombinant DNA technology utilizing yeast host systems and expression vehicles that synthesize, process and secrete heterologous protein as discrete product unaccompanied by interfering amounts of unwanted presequence or other artifact of expression.

Proteins that are secreted through the cell membrane are ordinarily produced in the cell as a transient preprotein (or "presecretory" protein). In that form, the protein contains an additional peptide sequence which presumably assists it in transversing the cell membrane. This additional sequence, referred to as a "signal peptide", is believed to be clipped from the secreted "mature" protein during the secretion processes by a membrane associated endopeptidase called "signal peptidase". Although the signal peptides of secretory proteins share some similarities, e.g. a short side chain amino acid at the carboxyl end and a hydrophobic central portion, their primary structures differ considerably. The signal peptides for a given organism also exhibit this variation. For example, the signal for human growth hormone is substantially different from the signal for human insulin. This suggests that each protein has evolved with a signal sequence which is particularly well suited to translocating the protein through the membrane.

This invention is based upon the discovery that a mature protein is secreted by yeast when the DNA encoding the heterologous protein is operably attached to the DNA sequence of a promoter homologous to yeast and the signal peptide coding portion of a signal homologous to yeast, for example, from the yeast invertase gene. In some cases, the yield of mature protein is higher than is obtained when the protein is expressed with its natural signal peptide (a heterologous signal relative to yeast) and the fidelity of processing is sometimes improved. Thus, this invention is directed to the means and methods of obtaining useful quantities of heterologous protein from the medium of a yeast culture containing DNA encoding the protein wherein the DNA coding for the heterologous protein is operably connected to a DNA sequence comprising a promoter and the signal portion of yeast homologous sequences. Of enormous advantage is the enablement, by this invention, of obtaining useful, discrete protein product in the cell culture medium by expression of heterologous DNA in an easily modified plasmid.

The publications and other materials referred to herein to illuminate the background of the invention, and in particular cases, to provide additional detail respecting its practice are incorporated herein by reference, and for convenience, are numerically referenced and grouped in the appended bibliography.

BACKGROUND OF THE INVENTION

Yeast organisms naturally transport a small number of certain homologous proteins to and sometimes through the plasma membrane as an essential contribution to cell surface growth and cell metabolism. As the cell buds as an incident of reproduction preparatory to formation of a daughter cell, additional proteins are required for formation of cell wall and plasma membrane as well as for metabolism. Some of these proteins are transported to the site of function, via a secretory pathway (1). Certain homologous proteins involved in the above processes are formed by translation in the rough endoplasmic reticulum (RER). During their biosynthesis, the signal peptide was thought to interact with a presumed particle called the signal recognition particle (SRP) which in turn recognizes a presumed RER membrane protein called SRP receptor or docking protein and subsequently the proteins are transferred across the RER membrane (2-4). Once proteins are segregated into the lumen of RER, they migrate to the Golgi apparatus and then to the vesicles. Fusion of the vesicles with the plasma membrane (by exocytosis) results in discharge of the vesicular contents (proteins) into the periplasmic space located between the plasma membrane and the cell wall. A small number of homologous proteins seems to be exported completely through the cell wall, such as $\alpha$-factor and killer toxin (5,6).

Nonetheless, the entire set of secretion processes is not yet fully understood in yeast. The presumed SRP of yeast may not be identical to the counterpart in mammalian cells. In other words, some heterologous signals (other than yeast signals) may or may not bind the yeast SRP with the same fidelity as those homologous (yeast) signals in the expression of the heterologous genes. Likewise, it is still uncertain whether modifications of proteins in vivo (such as phosphorylation, glycosylation etc.) assist the translocation of secretory proteins along the secretion pathway.

It was contemplated that recombinant DNA technology could provide valuable assistance in answering the open questions about the secretory process in yeast organisms. Given its proven applicability in enabling such, and other, organisms to produce copious quantities of heterologous polypeptide products endogenously (see, e.g., 7 to 17), it was thought that such technology would be helpful in achieving appropriate manipulation of the yeast host so as to direct the secretion of heterologous protein in discrete, mature form. This has, in fact, been achieved and is the subject of copending application Ser. No. 438,236, supra. In that application is described the discovery that a heterologous protein, initially expressed as a preprotein with its native signal (human) or hybrid thereof, can be secreted by yeast as a mature protein.

SUMMARY OF THE INVENTION

This invention is based upon the discovery that yeast organisms can be caused to express the genes for, process and secrete protein that is normally heterologous to yeast organisms so that the protein can be obtained from the supporting medium in discrete form unaccompanied by unwanted presequence or other artifact of expression. This is accomplished by expressing a DNA sequence encoding the heterologous protein linked to a DNA sequence encoding a homologous (yeast) signal sequence preferably that of invertase. Suitable yeast cells in a viable culture are transformed with expression vehicles harboring DNA encoding a heterologous protein operably connected to the DNA encoding, for example, the invertase signal peptide and a promoter, e.g., the promoter of the invertase gene. Upon production of the fusion protein containing the homologous signal peptide, the product is processed and the mature heterologous protein is exported into the medium of the cell culture. The product is removed with relative ease from the medium, without need to disrupt the viable yeast cells, and recovered in otherwise mature form for use without need to remove unwanted presequence or other artifacts of expression (e.g., the methionine which is sometimes attached to the otherwise N-terminal amino acid as a consequence of an inserted AUG translation start codon). Since the medium can be obtained in a form substantially free of viable or disrupted (i.e., lysed or otherwise broken) cells and contains the desired product, more easily employed purification techniques can be used. The mature protein product, after purification, is fit for use as intended. For example, human leukocyte interferon product finds use as a human antiviral and/or antitumor agent (see, generally, 7 to 17).

In summary, the present invention is directed as a primary aspect, to the means and methods employed in the production of a protein normally heterologous to yeast in discrete form, unaccompanied by presequence or other artifact of expression. In the context of this invention, expression processing and secretion are accomplished by placing a DNA sequence encoding a heterologous protein under the control of a promoter homologous to yeast, and in translational reading frame with a DNA sequence encoding a signal sequence homologous to yeast. Further, this invention provides yeast cultures capable of producing such protein and resultant yeast culture media containing such protein as product.

The term "invertase signal peptide" refers to an amino acid pre-sequence normally associated with invertase. "Homologous signal" means the signal peptide regions of yeast proteins which correspond at least substantially to the naturally occurring signals. Therefore, such signal regions may differ from the natural signals by the inclusion or exclusion of amino acids which do not materially affect its ability to function as a signal peptide. "Heterologous signal" refers to the signal peptide regions performing similar functions in organisms other than yeast.

By the term "heterologous protein" as used herein is meant protein that is not normally produced by or required for viability of a yeast organism. This term contemplates the functional insertion of DNA encoding such protein, via recombinant DNA technology, into an expression vehicle, in turn used to transform a yeast organism host. Functional insertion of DNA denotes the insertion of DNA encoding the heterologous protein into an expression vector under control of a promoter system. When this DNA sequence is operably connected to the DNA sequence coding for a homologous (to yeast) signal peptide, a hybrid preprotein, i.e., one which comprises the yeast signal peptide fused to the heterologous protein, is obtained. Examples of such heterologous protein are hormones, e.g., human growth hormone, bovine growth hormone, etc.: lymphokines; enzymes; interferons, e.g., human fibroblast, human immune and human and hybrid leukocyte interferons, bovine interferons etc.; viral antigens or immunogens, e.g., foot and mouth disease antigens, influenza antigenic protein, hepatitis core and surface antigens, etc.; and various other polypeptides, e.g., rennin, human serum albumin, human insulin, human insulin-like growth factor-1, various glycoproteins, etc.

"Secretion" as used herein means exportation of product through the plasma membrane and at least into or through the cell wall of the yeast organism into the medium supporting the cell culture. In this connection, it will be understood that in some instances, "secreted" product associates in some manner with the cell wall, perhaps necessitating a different purification procedure or a modification of the structure and function of the yeast host. "Processing" means the cellular cleavage of the homologous signal peptide from the mature protein so as to produce the heterologous protein unaccompanied by extraneous peptide in—so-called—discrete or mature form. By extraneous peptide is included peptide artifacts of expression such as methionine, as noted above. Processing admits of inconsequential cleavage of the signal peptide at a locus not inactivatingly near the precise point of signal peptide union with mature protein.

BRIEF DESCRIPTION OF THE DRAWINGS

FIG. 2 shows the nucleotide and amino acid sequences of the invertase signal and a portion of invertase and compares it to the expected and observed sequences for the invertase signal joined to LeIFA.

FIG. 13 shows the DNA sequence of the *Saccharomyces cerevisiae* invertase gene and its flanking regions (4.0 kb).

FIG. 14 illustrates plasmid pYEp9T-YIR (or L).

DETAILED DESCRIPTION OF A PREFERRED EMBODIMENT

Figure 1:
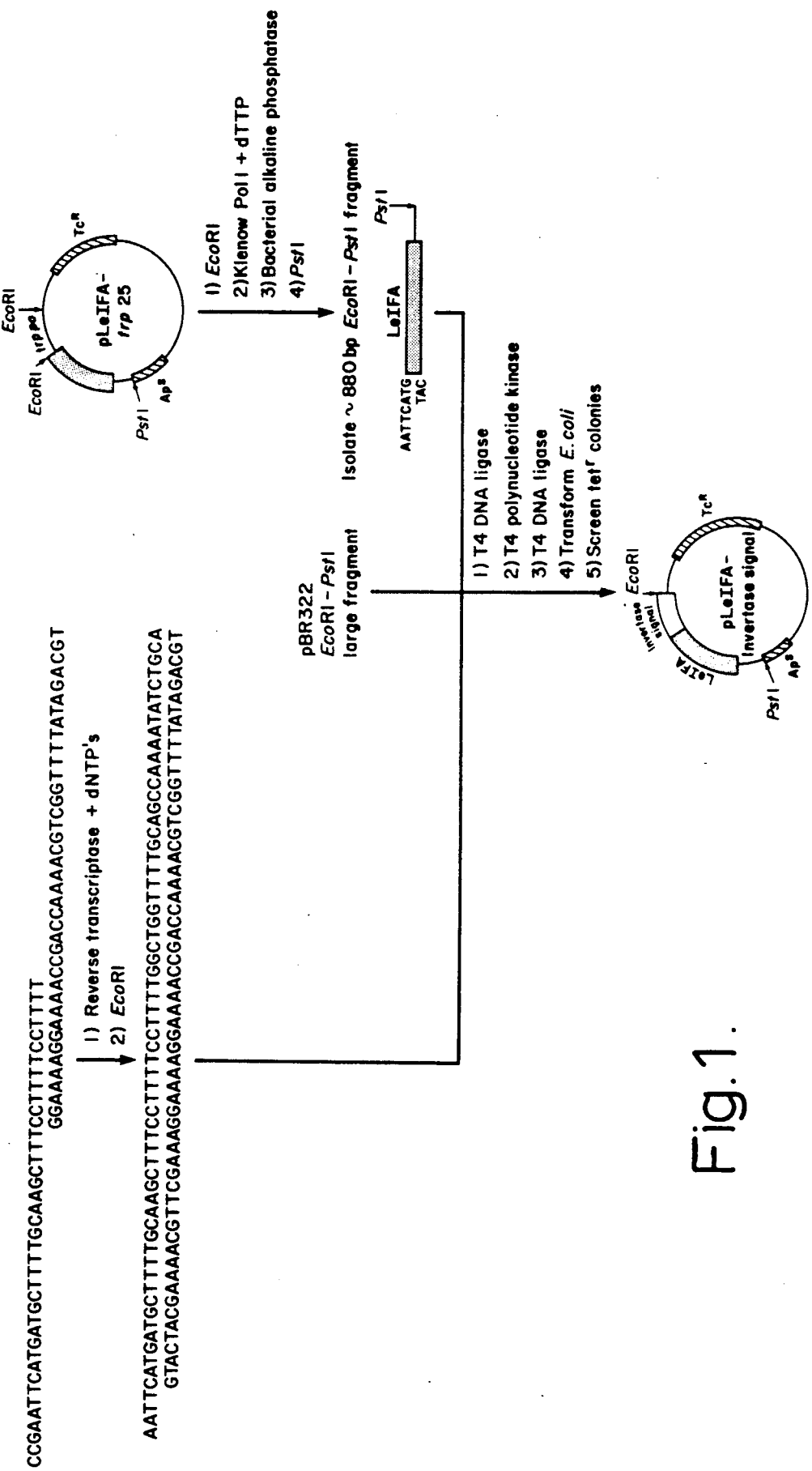
FIG. 1 illustrates the scheme for constructing a plasmid coding for the invertase signal and mature form of methionine-LeIFA.

Two basic strategies were adopted in order to obtain an expression vehicle according to the present invention, i.e., a vehicle comprising the DNA sequences of a promoter and of the homologous signal peptide of invertase operably connected in translational reading frame to a DNA sequence coding for a mature protein heterologous to the yeast organism.

In one strategy, the DNA sequence coding for the invertase signal was obtained synthetically and joined to the PGK promoter and this hybrid promoter signal sequence was joined to a gene coding for the heterologous protein and inserted into a plasmid. In the second strategy, the gene for invertase was isolated from a bank of yeast genomic DNA using hybridization techniques. The portion of the gene coding for invertase was removed and the DNA coding for the heterologous protein joined to the invertase promoter and signal coding DNA sequence. The details of these operations are described below, the heterologous protein chosen to exemplify the invention being human leukocyte interferon (LeIFA).

A. Expression In Yeast of Heterologous Protein Using Expression Vehicle With Hybrid Promoter-Invertase Signal 1. Materials and Methods Sources of DNA All DNA restriction enzymes, *E. coli* DNA polymerase large fragment (Klenow polymerase I) (18), T4 DNA ligase, and avian myeloblastosis virus (AMV) reverse transcriptase, were products of either New England Biolabs or Bethesda Research Laboratories and were used according to the prescribed recipes. The deoxynucleotide triphosphates dATP, dGTP, dCTP, and dTTP were purchased from PL Biochemicals. Plasmid LeIFA trp25 was obtained as described by Goeddel et al. (7).

Bacterial and Yeast Strains

*E. coli* K-12 strain 294 (endA thi⁻hsr⁻hsm⁺; ATCC 31446) (22) and yeast strain pep4-3 (20B-12 dtrpl pep4-3; ATCC 20626) (23) were used for transformations.

Growth Media

*E. coli* was grown in LB medium (25) which contained 1 percent Bacto-tryptone, 0.5 percent Bacto-yeast extract, and 0.5 percent NaCl. Drug (20 μg/ml of ampicillin or tetracycline) was added for growth of the plasmid-harboring bacteria.

Yeast minimal medium plates contained 0.67 percent Bacto-yeast nitrogen base without amino acids, 2 percent glucose and 3 percent Difco-agar. The minimal medium was used for yeast transformation with the addition of 1M sorbitol. YNB+CAA medium is the minimal medium supplemented with 10 mg of adenine, 10 mg of uracil and 5 grams of Difco-casamino acids (CAA) per liter. YEPD medium contained 1 percent Bacto-yeast extract, 2 percent Bacto-peptone and 2 percent dextrose (glucose).

Transformations

*E. coli* strain 294 was transformed according to a published procedure (19). Yeast strain pep4-3 was transformed by the method of Hinnen et al. (21).

Preparation of DNA

Plasmid DNAs from individual *E. coli* transformants were miniscreened by the method of Birnboim and Doly (20). This method has also been employed for large scale preparation of plasmid DNAs except they were further fractionated on a Bio-gel A-50 m (100–200 mesh; Bio-rad) column chromatography. DNA restriction fragments were isolated by electroelution from the gels, followed by phenol/chloroform extraction and ethanol precipitation. Two 40 mer oligodeoxynucleotides were chemically synthesized using the phosphotriester method (38).

Gel Electrophoresis

Polyacrylamide and agarose gel electrophoresis for plasmid DNAs were performed as described by Maniatis et al. (24) and by Sharp et al. (30), respectively. Sodium dodecyl sulfate-polyacrylamide gel electrophoresis for proteins was performed as described by Laemmil (31).

Design of Oligonucleotides Coded for the Invertase Signal Peptide

Two 40 mer oligonucleotides were designed as shown in FIG. 1, based on the known nuclueotide sequence coding for the yeast invertase signal region shown in FIG. 2. An additional ATG just preceding the ATG initiation site of translation was retained as the original nucleotide sequence of yeast invertase. A convenient EcoRI restriction site was placed in front of the ATGATG with two additional nucleotides (CC) at the 5'-end. These two oligonucleotides have twelve base pairs complementary to each other at their 3'-ends. After repairing these oligonucleotides with the reverse transcriptase, the 3'-ends of newly formed double strand DNA becomes a blunt end which will be ligated to a blunt end of a mature methionine-LeIFA maintaining the same coding frame. The 5'-end becomes a sticky end after EcoRI digestion.

Construction of a Plasmid (pLeIFA-Invertase Signal) Coding for the Invertase Signal-Mature Leukocyte Interferon A The scheme for construction of a plasmid coding for LeIFA bound to the invertase signal is shown in FIG. 1.

The AMV reverse transcriptase was used for the repair reaction of two synthetic oligonucleotides. 400 ng of two individual 40 mer oligonucleotides were placed in a 50 μl reaction volume containing 50 mM Tris-HCl, pH 8.0, 50 mM KCl, 6 mM MgCl₂, 1 mM dithiothreitol, 0.2 mM each of dATP, dGTP, dCTP, 150 μci of α-$^{32}$P-dCTP (New England Nuclear), and 25 units of reverse transcriptase (BRL). The reaction was continued at 42° C. for 75 minutes, and then terminated by phenol/chloroform extraction. The twice extracted aqueous phase was adjusted to 0.3M with 3M of sodium acetate at pH 5.5 followed by a 66 percent ethanol precipitation at −20° C. The precipitated, repaired DNA was digested with 200 units of EcoRI in a high salt buffer (50 mM Tris-HCl, pH 7.4, 10 mM MgSO₄, 1 mM β-mercaptoethanol and 100 mM NaCl) at 37° C. for 3 hours and then run on a 10 percent polyacrylamide gel.

After electrophoresis, the wet gel was placed on the top of a glass plate, covered with a sheet of Saran Wrap and exposed directly with a sheet of Kodak film (X-Omat AR-2) for 20 minutes. After autoradiography, the uppermost radioactive band (containing the invertase signal codons) was localized with the aid of the autoradiogram, excised from the wet gel and electroeluted in a dialysis bag. The eluted DNA was extracted twice with phenol/chloroform and subsequently precipitated with ethanol. DNA was then lyophilized to dryness and suspended in 10 μl of distilled water.

Plasmid LeIFA trp25, an *E. coli* expression plasmid, contains the structural gene for mature methionine-LeIFA (7) which is within a EcoRI-PstI fragment and does not have its natural signal codons. This plasmid DNA (7 μg) was first cut with 4 units of EcoRI in a 20 μl reaction volume containing a medium salt buffer which is the same as the high salt buffer described above, except that 50 mM instead of 100 mM NaCl was used. The EcoRI site was located just preceding the ATG initiation codon of mature methionine-LeIFA. In order to generate a right coding frame for mature methionine-LeIFA after its ligating with the invertase signal codons, a nucleotide G at the 3'-strand of the EcoRI site must be eliminated. Thus, the EcoRI fragment (containing methionine-LeIFA gene) was incubated with 3 units of DNA polymerase I large fragment in the presence of 25 μM dTTP at room temperature for 30 minutes. The presence of dTTP in the reaction is to prevent further removal of 3'-nucleotide by 3'-exonuclease activity of DNA polymerase I Klenow fragment from the coding frame of methionine-LeIFA. The reaction mixture was then phenol/chloroform extracted and ethanol precipitated. Dried DNA was resuspended in 30 μl of 10 mM Tris-HCl, pH 8.0, and 200 units of bacterial alkaline phosphatase was added. Reaction was incubated at 65° C. for 7 hrs. and then terminated by twice phenol/chloroform extraction and ethanol precipitation. The DNA was suspended in the medium salt buffer, digested with 2 units of PstI for 2 hrs at 37° C., and then loaded on a 6 percent polyacrylamide gel. The ~810 bp EcoRI-PstI fragment was isolated from the gel, electroeluted, phenol/chloroform extracted and ethanol precipitated.

2 μg of plasmid DNA (pBR322) (34) was digested in a 50 μl reaction volume of the medium salt buffer for 2 hrs at 37° C. with 10 units of EcoRI and 10 units of PstI. A large fragment (3.6 kbp) was isolated from the 5 percent gel and used as a vector fragment which has the tetracycline resistant gene. 20 ng of this EcoRI-PstI vector fragment was combined with the 65 bp of the invertase signal codons and the ~880 bp fragment of methionine-LeIFA constructed above. Reaction was incubated in 10 μl of 50 mM Tris-HCl, pH 7.6, 10 mM MgCl$_2$, 20 mM dithiothreitol, 1 mM ATP and 1 unit of T4 ligase (BRL) at room temperature for 16 hrs. Then the reaction mixture was diluted to 20 μl with the above ligation buffer and 5 units of T4 polynucleotide kinase was added followed by an incubation at 37° C. for 30 minutes. The reaction mix was cooled to room temperature and 2 more units of T4 DNA ligase was added. Reaction was further incubated at room temperature for another 16 hrs. This entire ligation mix containing pLeIFA-invertase signal was then used to transform competent *E. coli* 294 to tetracycline resistance on LB medium plates. Thirty tetracycline-resistant colonies were obtained.

Screening and Sequencing of Clones

Individual *E. coli* transformants were grown in 5 ml of LB medium containing 5 μg/ml of tetracycline for 16 hrs at 37° C. Plasmid DNAs from these transforming cells were prepared by a quick screen procedure (16) and suspended in 50 μl of distilled water. Ten microliters of plasmid DNA from each transformant was then digested with both EcoRI and PstI in the medium salt buffer at 37° C. for 3 hrs. and loaded on a 5 percent polyacrylamide gel. Six clones among those transformants contained a ~880 bp EcoRI-PstI fragment having both the invertase signal codons and mature methionine-LeIFA gene. Plasmid (pLeIFA trp25) DNA was also included as a control experiment which generates a ~810 bp EcoRI-PstI fragment bearing mature methionine-LeIFA gene. Thus, the EcoRI-PstI fragments derived from six clones were isolated and cloned into a sequencing phage M13MP9. The nucleotide sequence around the invertase signal codons, as well as the junction between the invertase signal codons and methionine-LeIFA gene, were then determined by the dideoxy sequencing method (32, 33). Two promising clones (designated E3 and F2) were obtained.

Figure 3:
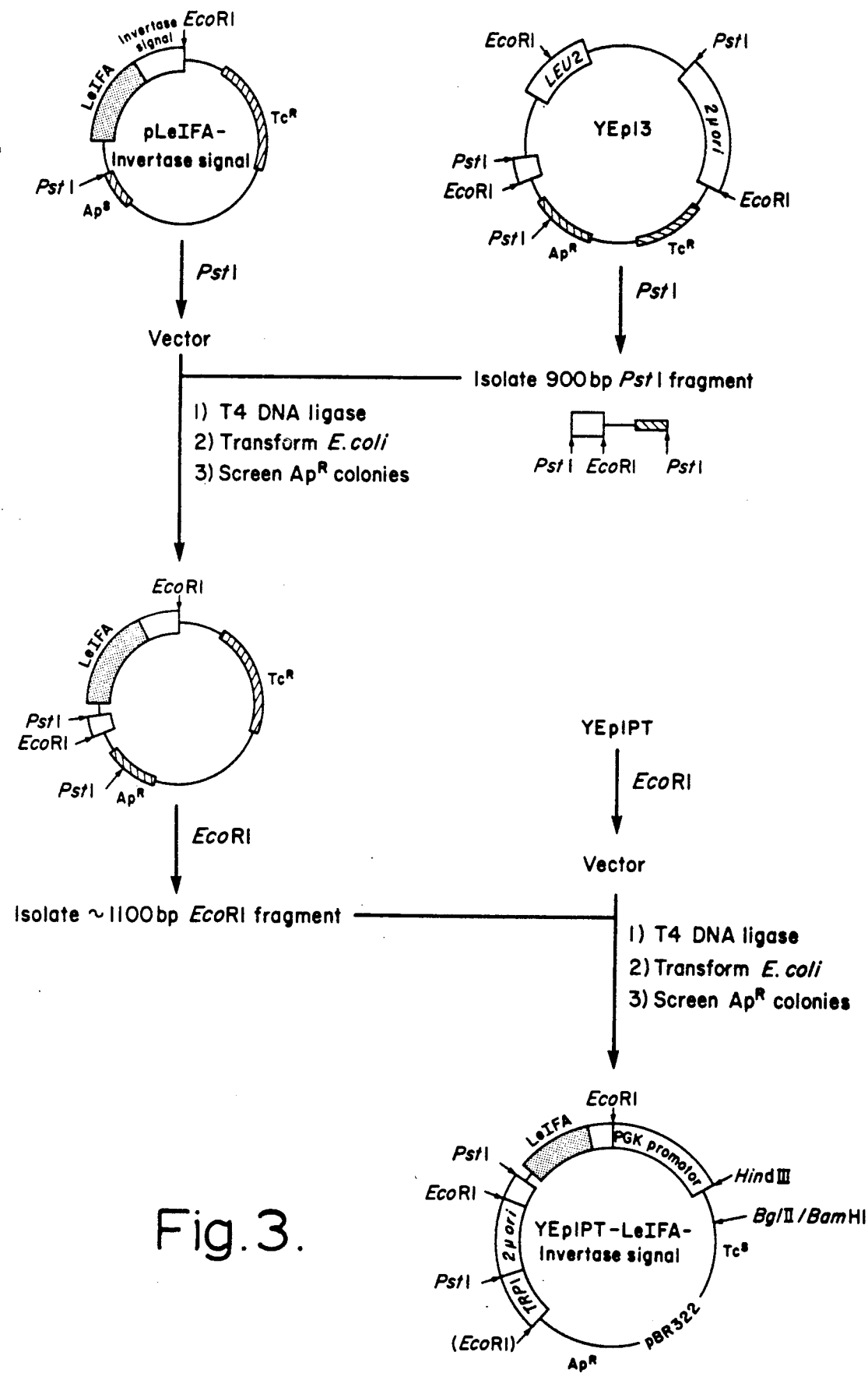
FIG. 3 illustrates construction of a plasmid for insertion into yeast to express LeIFA fused to an invertase signal.

Modification of the Invertase Signal-LeIFA DNA into an EcoRI Fragment for Insertion into a Yeast Expression Plasmid YEp1PT Plasmids for expression of LeIFA in yeast derived from clones E3 and F2 were constructed as shown in FIG. 3.

Plasmid DNAs from the clones E3 and F2 were linearized with PstI. The PstI end of this vector fragment was then converted to an EcoRI site by using an adaptor fragment (900 bp) isolated from a yeast plamid YEP13 (37). This adaptor fragment contains an internal EcoRI site and has PstI sites on both ends; the 247 bp of PstI to EcoRI is derived from yeast 2μ DNA and 654 bp of EcoRI to PstI is from PBR322. Thus, insertion of this 900 bp adaptor fragment into the PstI sites of those desired clone fragments resulted in the restoration of ampicillin resistance in plasmid harboring bacteria. The plasmid DNAs isolated from ampicillin resistant clones were cut with EcoRI and run on a 5 percent polyacrylamide gel. The ~1100 bp EcoRI fragment was electroeluted from the gel, extracted with phenol/chloroform and precipitated with ethanol.

A yeast expression plasmid YEp1PT (35) was digested with EcoRI and then treated with 1 unit of calf thymus alkaline phosphatase (Boehringer Mannheim) for 10 min at 37° C. The treated DNA was extracted once with phenol/chloroform and then precipitated with ethanol. 10 ng of this vector fragment was ligated with 150 ng of the invertase signal codons-LeIFA gene fragment (EcoRI), described above, for 15 hrs at 14° C. The ligation mix was used to transform *E. coli* strain 294. Plasmid DNAs from individual transformants were isolated and the orientation of the invertase signal codons-LeIFA gene to the PGK promoter on the vector was determined by restriction patterns of the DNAs. The desired plasmid DNAs, YEp1PT-LeIFA-invertase signal, derived from clones E3 and F2 were used to transform yeast strain pep4-3.

Preparation of Yeast Extract and Interferon Assays a. Extract Preparation

Cells of yeast strain PEP4-3 transformed by YEp1PT-LeIFA-invertase signal derived from clones E3 and F2 were grown in a ten liter fermentor at 30° C. in 2.6 percent yeast nitrogen base and 1 percent glucose to an $A_{550}$ of 3-4. At such cell density the initial 1 percent glucose was completely exhausted; cells were then slowly fed with glucose until $A_{550}$ reached 50–100. For assay each 10 ml aliquot was drawn and centrifuged at 10,000 rpm for 10 minutes in a Sorval RC38. The supernate (media) was diluted 20 to 100 fold in PBS/BSA buffer (20 mM $NaH_2PO_4$, pH 7.4, 150 mM NaCl, 0.5 percent bovine serum albumin) immediately before the assay. The cells (about ten $A_{550}$) were resuspended in 0.4 ml 7M guanidine-HCl in an Eppendorf (1.5 ml) tube containing about 0.4 ml of glass beads (0.45 to 0.5 mm, B. Braun Melsurgen AG), vortexed twice for 2 minutes at the highest speed, and centrifuged in an Eppendorf centrifuge for 0.5 minute. The cell lysate was then diluted in PBS/BSA buffer as above for bioassays.

b Interferon Assays

Yeast extracts and media were assayed for interferon by comparison with interferon standard using the cytopathic effect (CPE) inhibition assay (26). Cells used in the assay were bovine kidney cells (MDBK).

"Western" Blots of the Human Leukocyte Interferons (LeIFA) Produced from Yeast

Both culture media and cellular extracts were precipitated with 10 percent ice-cold trichloroacetic acid. The precipitates were dissolved in 100 mM Tris-base, 20 mM dithiothreitol, 0.01 percent bromophenol blue and 20 percent sucrose at 37° C. for 30 minutes and boiled in a bath for 3 minutes. After cooling to room temperature, 100 mM of sodium iodoacetamide was added, further incubated at 37° C. for one hour, and then run on a 12.5 percent SDS-polyacrylamide gel until the tracking dye reached the bottom of the gel. Gel was soaked in electrophoresis buffer (without SDS) for 20 minutes and proteins on the gel were electrophoretically transferred onto a nitrocellulose paper in the same buffer at 0.5 Amp for 2 hours (E-C Apparatus Corp.). After transfer the nitrocelulose paper was incubated in NET buffer (50 mM Tris-HCl, pH 7.4, 150 mM NaCl, 5 mM EDTA, 0.25 percent gelatin (w/v) and 0.05 percent NP-40) overnight. The paper was rinsed briefly in water and put in a plastic bag. 10 ml of NET buffer and 150 μl of rabbit anti-LeIFA antiserum was added and incubated at room temperature for 3 hours. After extensive washes with water and NET buffer, the paper was incubated with 10 ml of NET buffer and 0.2 Ci of $^{125}$I-protein A (Pharmacia) for two hours. Then the paper was rinsed with a large volume of water over a period of 10 minutes, blotted dry, and exposed to Kodak X-ray film with intensifying screen at −70° C.

Purification of the Human Leukocyte Interferon (LeIFA) from Yeast Media

Yeast pep4-3 transformants containing plasmids derived from clones E3 and F2 were separately grown in 10 liter fermentor and after cell removal the media were separately purified as follows.

a. Invertase Signal-Containing Clone E3

Figure 5:
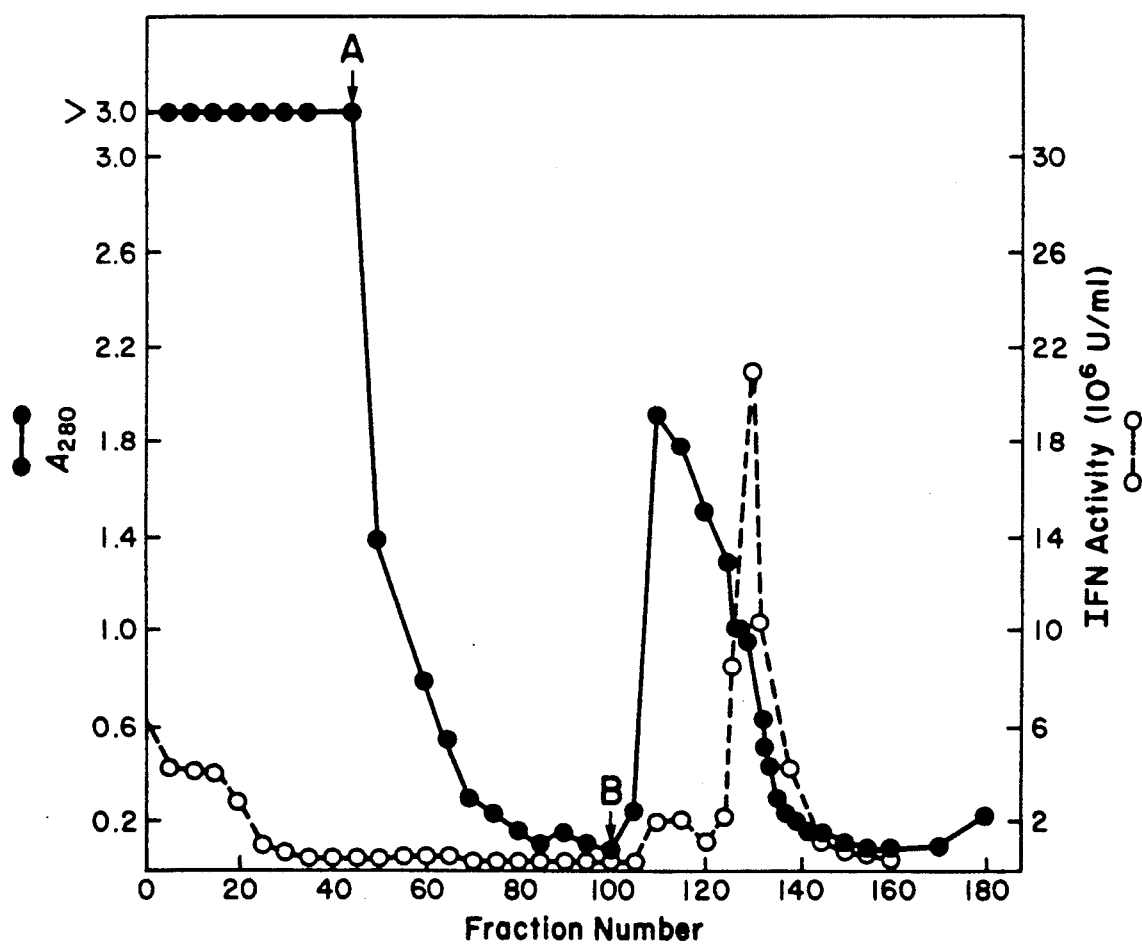
FIG. 5 shows carboxymethylcellulose (CM 52) column chromatography of media LeIFA from the yeast pep 4-3 strain containing a plasmid YEp1PT-invertase signal-LeIFA (E3). Letter A indicates the onset of washing column with 25 mM ammonium acetate, pH 5.0 and B shows the start of elution with 0.5M NaCl.
Figure 6:
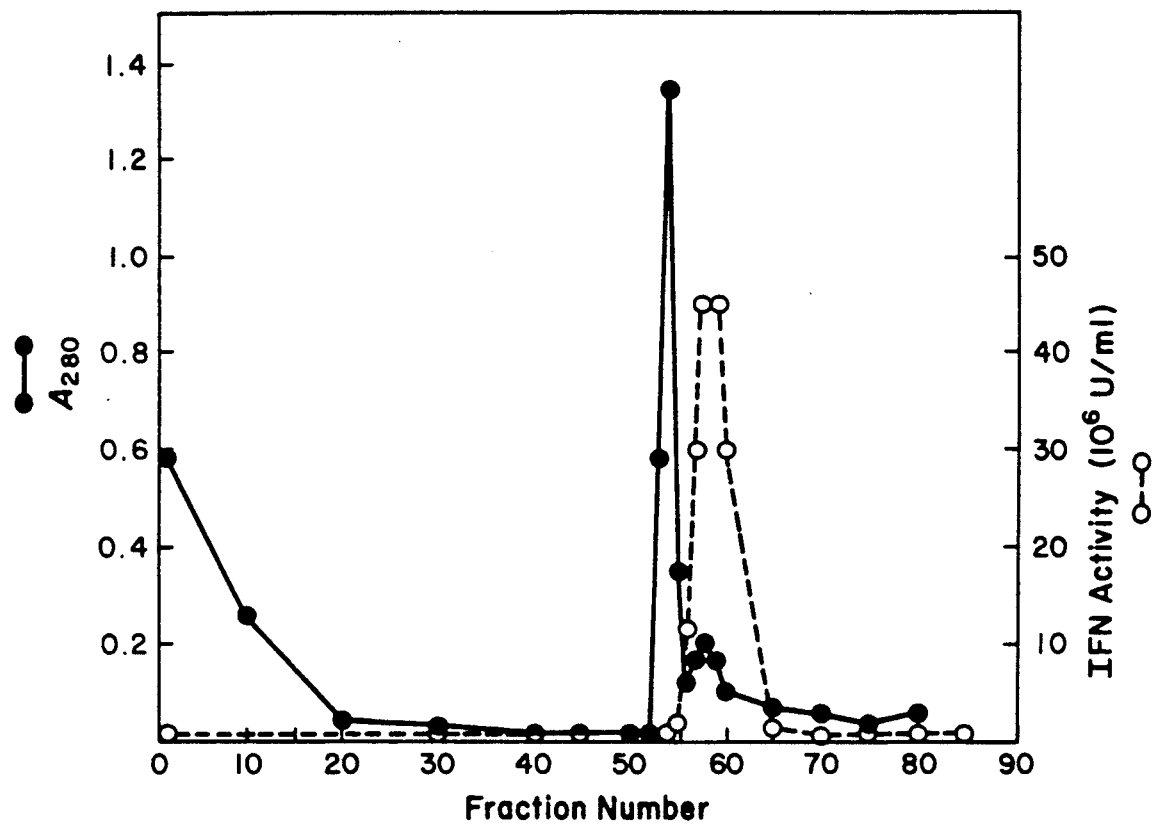
FIG. 6 shows immunoaffinity column chromatography of media LeIFA from the CM 52 column of FIG. 5.

Seven liters of the media were concentrated and diafiltered against five liters of 25 mM ammonium acetate, pH 5.0 in an Amicon thin-channel cell with reservoir (Amicon TCF 10-90 mm and RG-11) using a YM-5 membrane at 18 psi. During the concentration and diafiltration the retentate was transferred to a 2.5 liter Amicon stirred cell using a YM-5 membrane (150 mm) and 40 psi. A total of ten liters of 25 mM ammonium acetate was used in the diafiltration yielding a final retentate volume of 900 ml. The retentate was then diluted to 2 liters with ammonium acetate and passed over a CM52 column (500 ml bed volume) at 1.7 ml per minute. The column was eluted with 0.5M NaCl. Ten ml fractions were collected and assayed as described above (see FIG. 5). Fraction numbers 126–238 were pooled and dialyzed against 25 mM Tris-HCl, 10 mM EDTA, pH 8.0. The dialyzed pool (188 ml) was then passed over a 0.5 ml immunoaffinity column containing monoclonal antibody to LeIFA covalently bound to Affigel 10 (BioRad) at a flow rate of 0.15 ml per minute. The column was eluted with 0.2M acetic acid, pH 2.5. One ml fractions were collected and assayed (see FIG. 6). Fraction number 58 (4.5×10 units per ml) was further purified by high pressure liquid chromatography (HPLC) on a Synchropak RP-P column. The column was eluted at a flow rate of 1 ml per minute with a linear gradient of 0–100 percent acetonitrile in 0.1 percent trifluoroacetic acid (TFA). One ml fractions were collected and assayed (see lower panel FIG. 7). A 5 μg sample of LeIFA purified from E. coli was also chromatographed as a control (see the upper panel of FIG. 7). Fraction numbers 42 and 43 (5.6×10 units per ml) were pooled and sequenced.

b. Invertase Signal-Containing Clone F2

Eight liters of media were concentrated and diafiltered against six liters of ammonium acetate, pH 5.0, in a 2.5 liter Amicon stirred cell (Amicon 2000) using a YM-5 ultrafiltration membrane to a final volume of 1.7 liters. The concentrate was then diafiltered against six to eight liters of 25 mM Tris-HCl, 10 mM EDTA, pH 8.0, to a final volume of approximately 50 ml. The retentate was diluted to 530 ml and 430 ml was passed over a 1.0 ml immunoaffinity column containing a monoclonal antibody to LeIFA covalently bound to Affigel 10 at a flow rate of less than 10 ml per hour. The column was washed with 25 mM Tris-HCl, 10 mM EDTA, pH 8.0. The interferon activity was eluted from the column with 0.2M acetic acid. One ml fractions were collected and assayed (see FIG. 9). Fraction number 20 (4.0×10 units/ml) was further purified by HPLC on a Synchropak RP-P column. The column was eluted at a flow rate of 1 ml per minute with a linear gradient of 0 to 100 percent acetonitrile in 0.1 percent TFA, pH 2.5 (see the lower panel of FIG. 10). One ml fractions were collected and assayed. A 5 μg sample of purified LeIFA produced in E. coli was also chromatographed as a control (see the upper panel of FIG. 10). The interferon activity eluted from the column in a peak centered about fraction number 44 (9.0×10 units/ml). Fractions number 41 and 44 were pooled and sequenced as follows.

Amino-terminal Sequencing of LeIFA Purified from the Yeast Media

LeIFA isolated from the yeast medium was subjected to consecutive Edman degradations in the Beckman 890B sequencer (27) using the Quadrol Program. Two mg of Polybrene (poly N,N,N,N,-tetramethyl-N-trimethylenehexamethylene diammonium diacetate) was added to the sequencer cup as a protein carrier (28). The resulting 2-anilino-5 thiazolinone was added to 25 percent trifluoroacetic acid and heated to 70° C. for 10 minutes to convert it into the 3-phenyl-2-thiohydantoin (PTH derivative)(29). The PTH-amino acid residue was then dissolved in 50 percent acetonitrile and analyzed by a reverse-phase high-pressure liquid chromatography. Each PTH-amino acid was then identified by comparison to the retention times of a mixture of standard PTH-amino acids.

2. Results

Constructions of the Fused Invertase-Signal Codons and Methionine-LeIFA Gene

The invertase-signal codons were constructed from two synthetic oligonucleotides (40 mer) which complement each other at 12 base pairs as described in Materials and Methods and illustrated as in FIG. 1. The repairment of two complementary oligonucleotides by the AMV reverse transcriptase yielded a double strand of DNA (54 bp) with a blunt 3'-end and a sticky 5'-end after EcoRI restriction. Ligation of this invertase-signal codon and mature form of methionine-LeIFA gene (within a EcoRI-PstI fragment) from pLeIFA-trp25 to an EcoRI-PstI fragment of plasmid pBR322 (34) was accomplished after removal of a nucleotide G from the 3'-strand of the EcoRI site of methionine-LeIFA gene by the 3'-exonuclease of DNA polymerase Klenow fragment (see FIG. 1). The resulting hybrid plasmid designated as pLeIFA-invertase signal possessed a correct reading frame from the invertase-signal codons to the gene of mature methionine-LeIFA. Restriction analysis of thirty transformants containing pLeIFA-invertase signal showed 6 clones bearing the ~800 bp EcoRI-PstI fragment whereas the EcoRI-PstI fragment of mature methionine-LeIFA gene is ~810 bp (without the invertase-signal codons). Dideoxy DNA sequencing of these 6 clones showed 4 of them have a deletion of nucleotide(s) in the region of invertase-signal codons, rendering the invertase-signal codons and mature methionine-LeIFA gene out of coding frame relative to each other.

Two other clones (F2 and E3) were in right coding frame as shown in FIG. 2. Clone F2 coded for a fusion bearing an invertase-signal and methionine-LeIFA. The junction between the invertase-signal codons and methionine-LeIFA gene was as expected, whereas a trinucleotide GCC corresponding to an amino acid residue 15 (alanine) of invertase signal was deleted. This deletion probably resulted from an error in the synthesis of oligonucleotides coding for the invertase signal region.

Clone E3 coded for a fusion bearing an invertase signal and mature LeIFA. There is no ATG prior to the mature LeIFA gene of this clone. The reason for deletion of ATG (coded for methionine) is unknown. Presumably, the limited 3'-exonuclease digestion with the Klenow fragment of DNA polymerase I at the 3'-strand of the EcoRI site of methionine-LeIFA gene in the presence of 25 μM dTTP did not cease at T but rather proceeded three more nucleotides (see FIG. 1).

In order to express these two hybrid clones (F2 and E3) in yeast, the PstI site at the 3'-end of non-coding region of each of clones F2 and E3, was converted into an EcoRI site with a 247 bp adaptor fragment derived from yeast 2 micron DNA as illustrated in FIG. 3. This EcoRI fragment containing the invertase signal codons and LeIFA gene was inserted into a yeast expression plasmid YEp1PT (35). The resulting plasmids were designed as YEp1PT-LeIFA-invertase signal (F2 or E3). Thus, this expression plasmid contains a portion of pBR322 with the ampicillin resistance gene and the *E. coli* origin of replication for selection and stable growth in *E. coli*. It also contains a TRP1 gene allowing for selection in trp⁻ yeast and a 2 micron plasmid origin of replication allowing for replicating autonomously in yeast. In this plasmid, transcription of hybrid genes was under the control of the yeast 3-phosphoglycerate kinase (PGK) promoter.

Synthesis and Secretion of LeIFA by Yeast

A plasmid containing the natural signal codons of LeIFA in the yeast expression vector YEp1PT was previously constructed (35) and used here as a control for comparison of the level of production of LeIFA from the plasmid YEp1PT-LeIFA-invertase signal (F2 or E3). The activity of interferon from both cells and media were measured and shown in Table 1. Both expression and secretion of LeIFA in yeast were higher with the yeast invertase (a homologous signal-cell system) signal relative to the human natural signal (a heterologous signal-cell system). The interferon activity in the media was

TABLE 1

| Production of Human IFN-α2 in Yeast | | |
|---|---|---|
| | Am't of Cellular Interferon (mg/L) | Am't of Media Interferon (mg/L) |
| preLeIFA | 4.00 | 0.25 |
| F2 | 5.85 | 1.75 |
| E3 | 10.10 | 1.00 |

The interferon activity in the media was 4-fold higher in cells transformed with E3-containing plasmid and 7-fold higher in cells transformed with F2-containing plasmid in yeast strain pep4-3 than observed with the cells transformed with the plasmid coding for the natural LeIFA signal.

The Nature of LeIFA Produced from Yeast Containing F2 or E3 Plasmid

Figure 4:
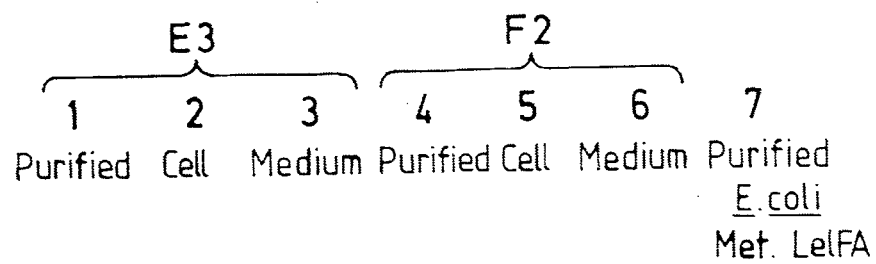
FIG. 4 Western blot of cellular and media LeIFA produced by transformed yeast.

To understand the nature of LeFIA produced by yeast, a "Wester" blotting procedure (36) was used. Both cellular and media proteins were separated by 12.5 percent SDS-polyacrylamide gel and subsequently transferred onto the nitrocellulose paper. The LeIFA was then detected by a rabbit antibody raised against LeIFA with radioactive protein A of *Staphylococus aureus*. As shown in FIG. 4, LeIFA from both cells and media migrated to the same position as mature methionine-LeIFA produced from *E. coli*. No additional radioactive band was detected. These results suggest that LeIFA was expressed and completely processed by yeast.

Figure 7:
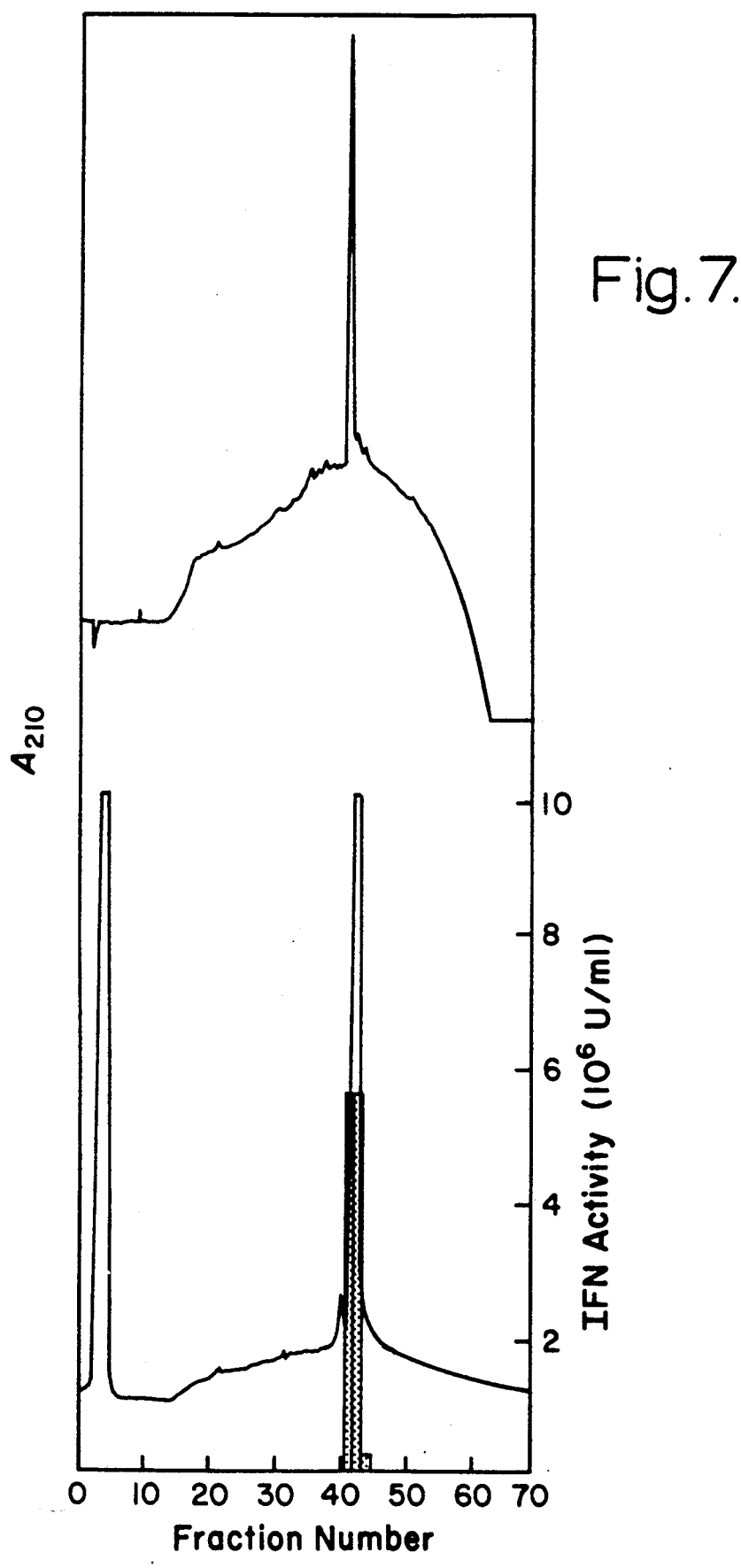
FIG. 7 illustrates high pressure liquid chromatography of media LeFIA from fraction number 58 of immunoaffinity column of FIG. 6. Methionine-LeIFA (5 μg) purified from E. coli was run as a control and shown on the upper panel of this figure.
Figure 8:
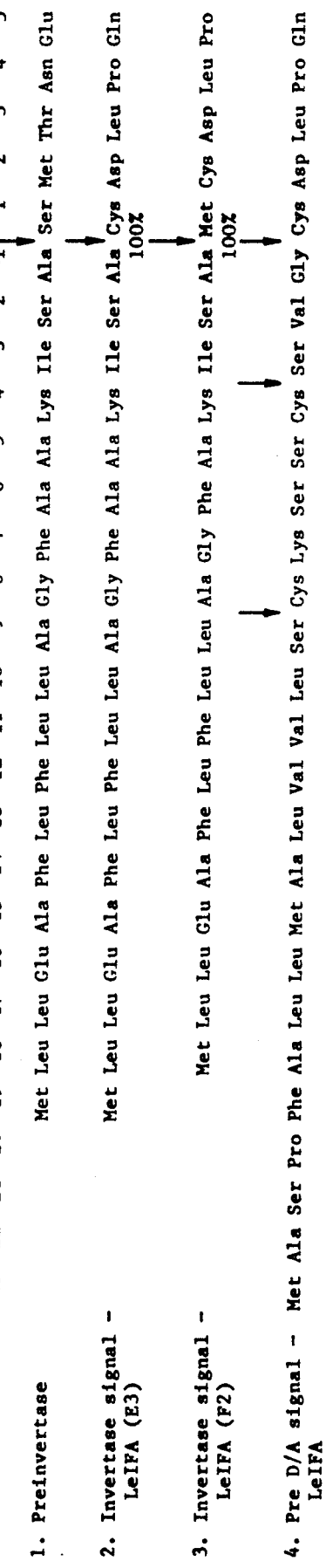
FIG. 8 shows the amino terminal sequences of LeIFA produced from plasmids containing fragments from clones F2 and E3.

To further ascertain whether LeIFA expressed from E3-containing plasmid was indeed properly processed, medium from yeast containing E3-plasmid was purified by a combination of carboxymethylcellulose (CM-52) chromatography (see FIG. 5), monoclonal antibody affinity chromatography (see FIG. 6), and high-pressure liquid chromatography (see FIG. 7). Gel electrophoresis in SDS of purified LeIFA showed a single commassive blue-staining band. Purified protein was subjected to 15 cycles of Edman degradations. As shown in FIG. 8, the amino-terminal sequence of purified LeIFA is identical to the known sequence of LeIFA, suggesting that the yeast signal peptidase not only recognizes the primary structure of the fused invertase-signal LeIFA but cleaves at the correct site to generate the natural mature form of human LeIFA.

Figure 9:
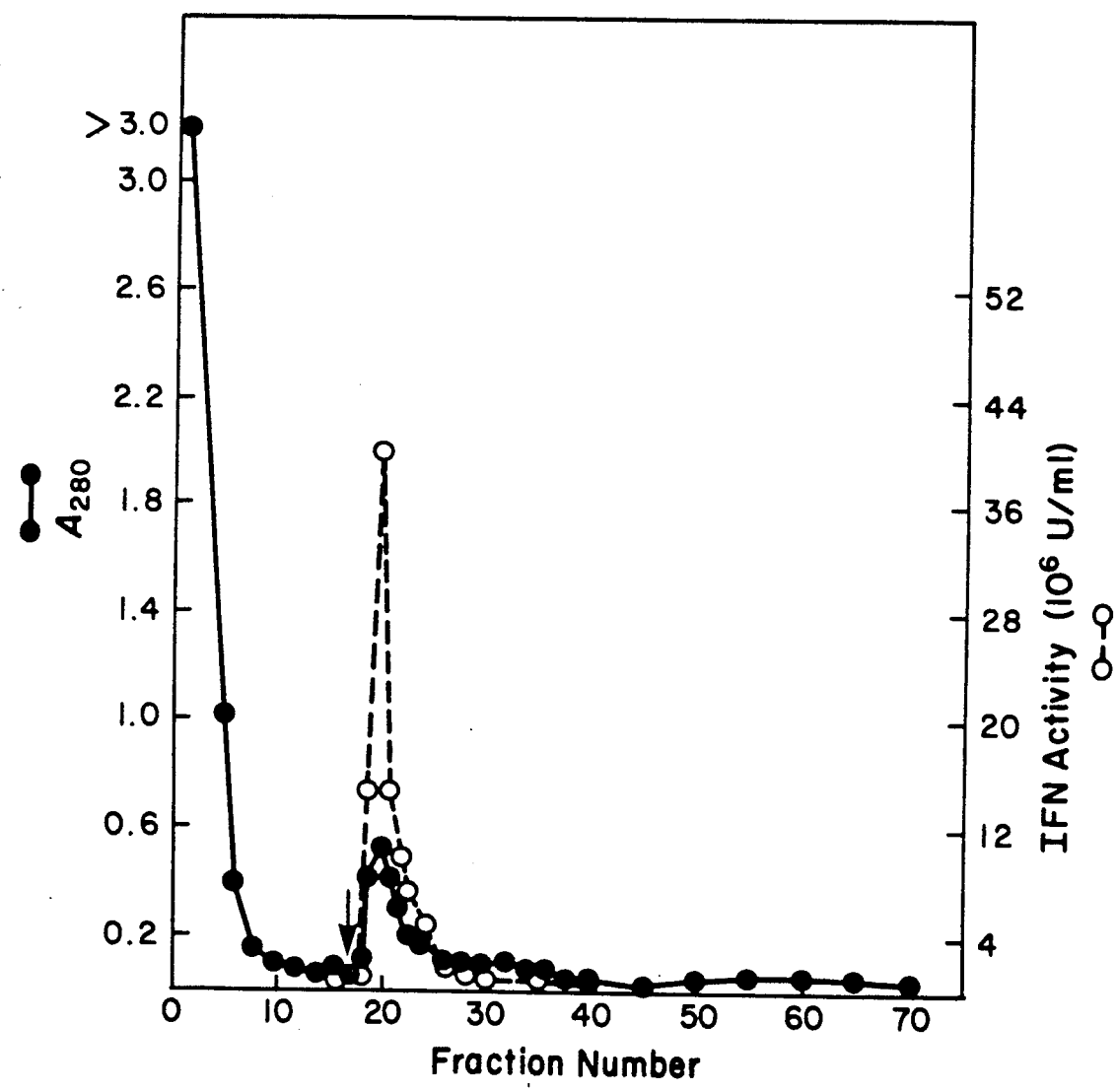
FIG. 9 shows immunoaffinity column chromatography of media LeIFA from the yeast pep 4-3 strain containing a plasmid YEp1PT-invertase signal-LeIFA (F2).
Figure 10:
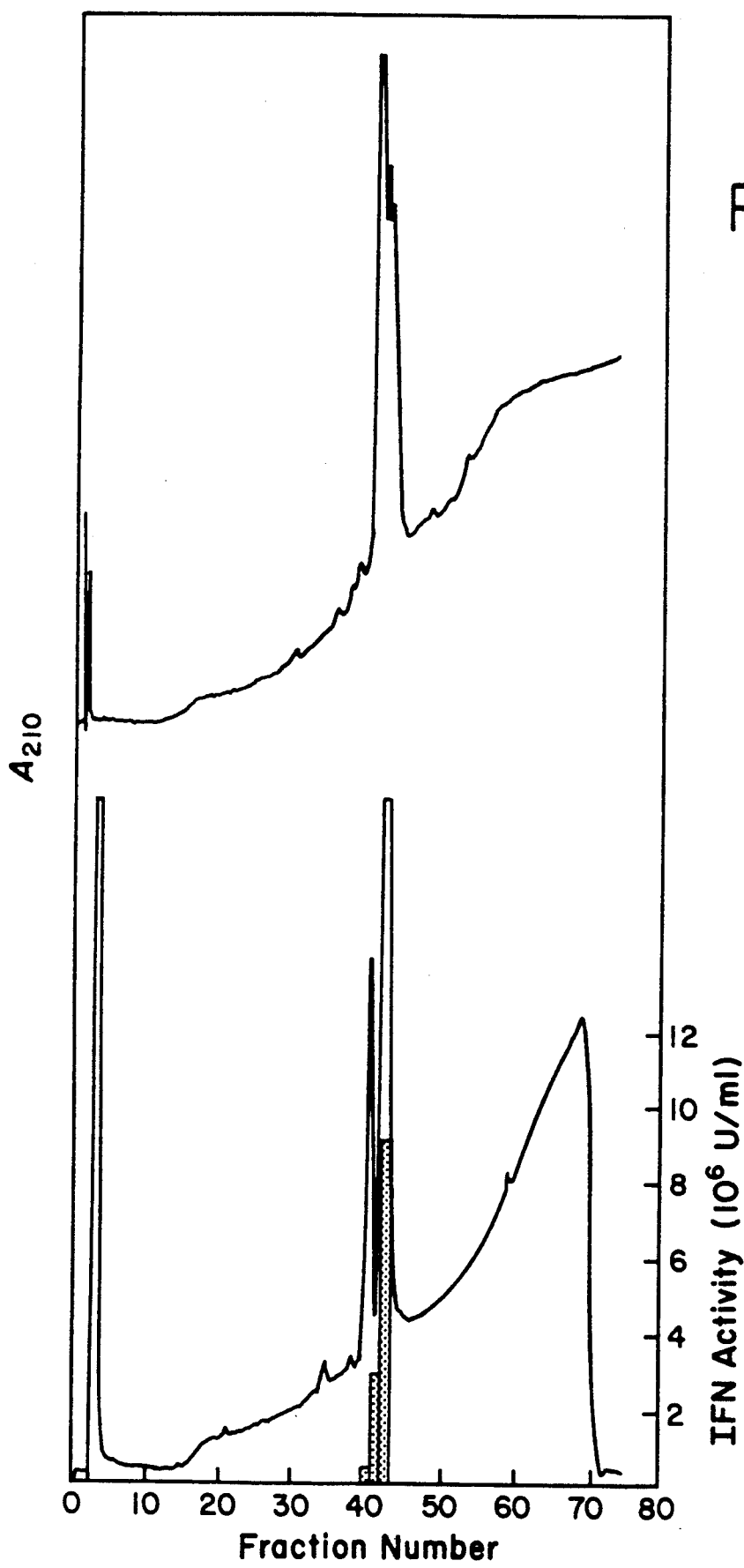
FIG. 10 illustrates high pressure liquid chromatography of media LeIFA from fraction number 20 of immunoaffinity column of FIG. 9. Methionine-LeIFA (5 μg) purified from E. coli was run as a control and shown on the upper panel of this figure.

Medium from yeast transformed with F2 containing plasmid was also purified in the same was as LeIFA from E3 except CM52 column chromatography was omitted (see FIGS. 9 and 10). Analysis of amino terminal sequence of purified LeIFA(F2) showed cleavage had occurred prior to the methionine residue of LeIFA (see FIG. 8). In both transformants, processing of the pre-LeIFA to remove the signal appears to be complete.

B. Expression in Yeast of Heterologous Protein using Expression Vehicle with Invertase Promoter and Signal 1. Materials and Methods

Construction of Yeast Genomic Library

Total genomic DNA was isolated from a yeast strain S17990 (αtrp5 his4 ade6 gal2) of Saccharomyces cerevisiae by the method of Smith and Halvorson (39). 370 μg of DNA was partially digested with 2.5 units of Sau3AI (New England Biolab) in 2 ml of reaction mixture. Aliquots were removed at 10, 20 and 30 min., chilled wand inactivated with 20 mM EDTA. The pooled, phenol-extracted DNA was fractionated by centrifugation in 10-50 percent sucrose gradients in 1M NaCl, 20 mM Tris-HCl (pH 8.0) and 10 mM EDTA. The Sau3AI fragments 15 kb determined by agarose gel electrophoresis were isoloated and inserted into the alkaline phosphatease-treated BamHI site of plasmid YRp7. The resultant ligated DNA was then used to transform E. coli strain 294. The transformants were individually picked and stored in 96 wells of tissue culture microtiter dishes (Costar, Cambridge, Mass.) at 20° C. in the presence of 10 percent dimethylsulfoxide in LB medium.

Synthesis of the Probe

The synthetic oligonucleotide (19 mer) probe corresponding to the signal peptide region of the invertase gene was prepared using the phosphotriester method (38). The nucleotide sequence is (5'-AAGCTTTCCTTTTCCTTTT-3') and was obtained from Dr. Marian Carlson, Department of Human Genetics, Columbia University, New York.

Isolation of Recombinant Plasmids

E. coli transformants of yeast genomic library were transferred and grown on fresh LB medium containing ampicillin at 20 μg/ml in the 96 well microtiter dishes overnight. Fresh cells were transferred onto the non-sterilized nitrocellulose filters (Schleicher and Schuell, BA85, 132 nm diameter) placed on S-agar plates (32 g tryptone, 5 g NaCl, 15 g Difco-agar and 0.2 g NaOH per liter) containing ampicillin (20 μg/ml) and allowed to grow for 6-8 hours at 37° C. At this time, cells formed a thin layer of colonies and filters were then transferred to another S-agar plate containing both ampicillin (20 μg/ml) and chloramphenicol (150 μg/ml). After 14 hours of amplification colonies were processed for hybridization by denaturing in 1.5M NaCl and 0.5M NaOH for 3 min., neutralizing in 3.0M NaCl, 0.5M Tris-HCl, pH 7.5, for 3 min., and finally washing in 6X SSC for 3 min. Filters were dried by air and baked in oven with vacuum at 80° for 2 hours.

Prehybridization was done by incubating the filters at 42° overnight with agitation in the prehybridization buffer (0.1M Tris-HCl, pH 7.5, 6 mM EDTA, 0.1 mM ATP, 1 mM sodium pyrophosphate, 1 mM sodium phosphate, 0.9M NaCl, 1X Denhardt's solution, 0.5 percent NP-40 and 0.1 mg/ml of E. coli tRNA). After prehybridization, filters were hybridized at 42° overnight in the fresh prehybridization buffer with the synthetic probe of $^{32}$p-labeled oligonucleotide (19 mer) described above. Filters were then washed three times in 6X SSC for 20 min. at 37° C. Dried filters were exposed to Kodak XR-2 X-ray film with DuPont intensifying screen at −80° C.

DNA Sequence Determiniation

DNA sequencing of the invertase gene and its flanking regions was done by the dideoxy-chain termination procedure (33, 40, 41) using the single stranded phage M13mp8 and M13mp9 and a synthetic phage-specific primer. Samples were separated by electrophoresis on 5 percent polyacrylamide/8M urea "thin" gels (42). Gels were dried onto Whatman 3 MM paper and exposed to Kodak X-ray film for varying lengths of time. The sequence of the Saccharomyces cerevisiae invertase gene and its flanking regions (4.0 kb) is shown in FIG. 13. The translated region encodes the preinvertase of 532 amino acid residues and of molecular weight 60,649. The potential glycosylation sites are underlined.

2. Results

Identification of Recombinant Plasmids Containing the Invertase Gene

Figure 11:
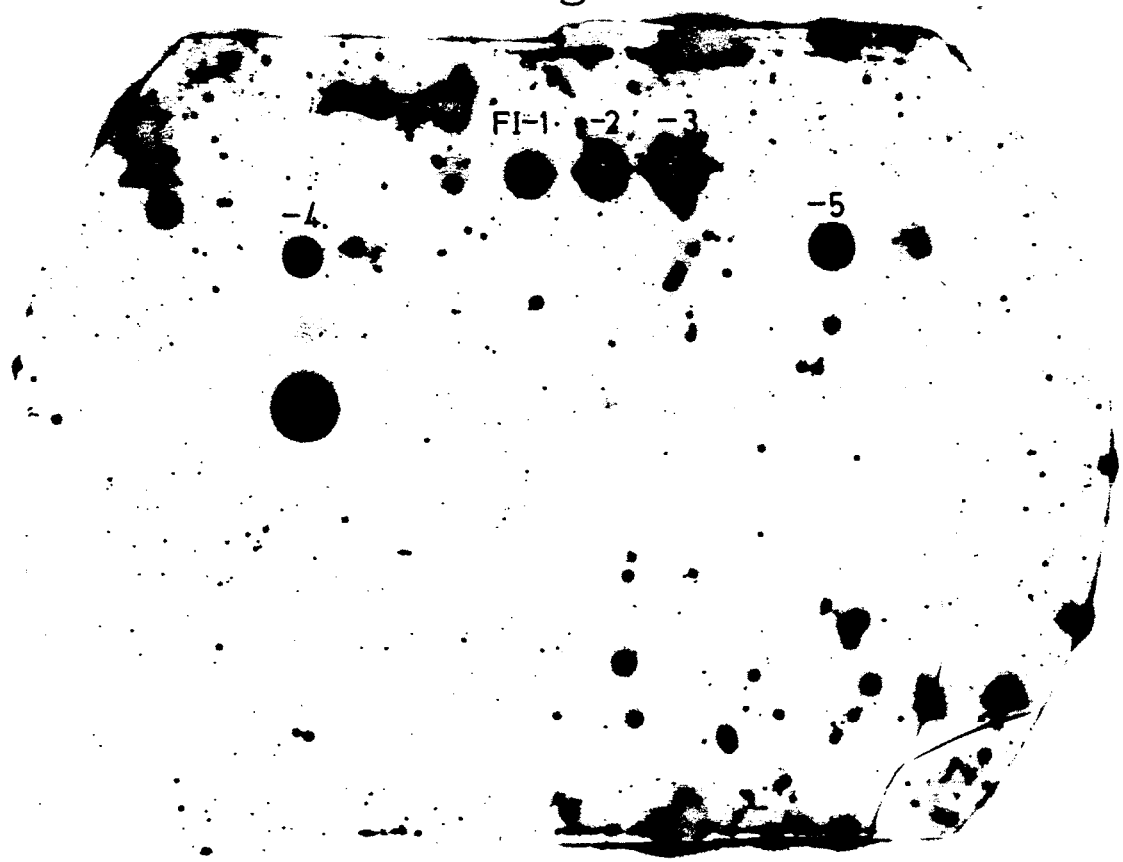
FIG. 11 illustrates screening of invertase gene containing colonies by hybridization of plasmid DNAs on the nitrocellulose filters with the probe.

Approximately 10,000 bacterial colonies form yeast genomic library were screened for in situ hybridizaton with 5'-$^{32}$p-labeled oligonucleotide (19 mer). Fifty-four colonies were hybridized to the probe. Plasmid DNAs from these fifty-four colonies were prepared by the method of Birnboim and Doly (20) and tested for hybridization with the same probe after spotting small amounts of DNAs onto a nitrocellulose filter. Five of the 54 plasmid DNAs were strongly hybridized (see FIG. 11) and designated as FI 1-5, respectively. Using the same 19 mer of oligonucleotide as a primer for DNA polymerase I (Klenow enzyme), these five plasmids were further verified by the supercoiled DNA sequencing method (40). All have identical DNA sequences for at least 180 base pair sequenced. The amino acid sequences deduced from this DNA sequence agrees well with the known partial sequence of invertase from residue 12 to 40 (43). These results indicate that these five recombinant plasmids contain part or all of the invertase gene.

Restriction Map of Recombinant Plasmids Containing the Invertase Gene

Figure 12:
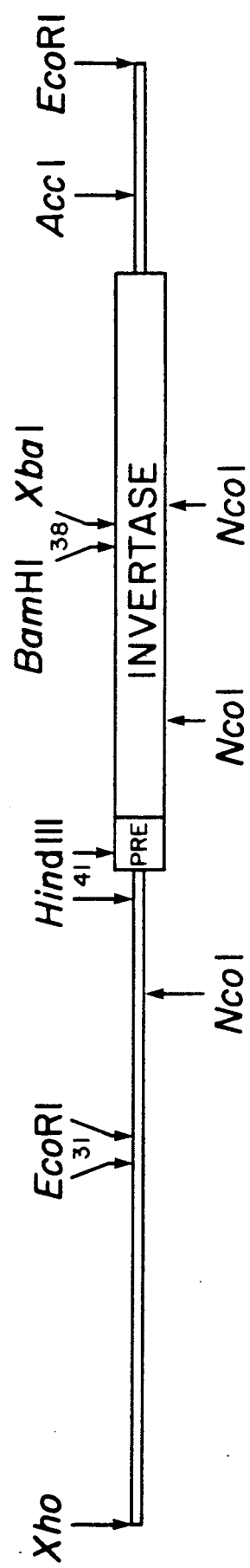
FIG. 12 is the restriction map of pFI4 inserted between XhoI and EcoRI (~5.5 kb).

To map the restriction sites of DNA inserts, plasmid DNAs prepared from clones FI 1-5 were analyzed by digestion with various restriction enzymes. One of the five clones (designated FI4) has the entire invertase gene and its restriction map is shown in FIG. 12. This map is identical to that reported by Carlson and Botstein (44).

Subcloning of Clone F14 and Expression of the Invertase from Subclones

A 4.0 kb EcoRI fragment containing the invertase gene isolated from clone FI4 (see FIG. 12) was inserted into a high copy number of yeast expression plasmid YEp9T which was constructed by replacement of the EcoRI-Hind III fragment of PGK promoter in YEp1PT (35) with the EcoRI-Hind III fragment of pBR322 (34) (FIG. 14). Two orientations of EcoRI fragment in the resulting recombinant plasmids were used to transform a yeast strain pep4. Cells were spun down and resuspended in either high glucose (5 percent) or low glucose (0.1 percent) containing medium for 1 hour. The invertase activity was measured as previously described (45). The level of expression of invertase in those transformants containing two different orientations of plasmids (designated YEp9T-YIR and YEp9T-YIL) was identical, which is about 20 times higher than the transforming strain pep4 at 1 hour of derepressed (0.1 percent glucose) condition (see FIG. 14). It is also interesting to note that production of the invertase in the transformants containing the invertase gene was not completely repressed under the repressed (5 percent glucose) condition but the wild type strain pep4 was.

Sequence of the Invertase Gene and its Flanking Region

The approximately 4 kb DNA fragment from XhoI To AccI of clone F14 was sequenced and shown in FIG. 13. The amino-terminal sequence of the invertase deduced from this DNA sequence agreed fully with the partial amino-terminal sequence reported by Perlman et al. (43). Furthermore, the last three amino acids in the carboxy-terminus are identical to the reported sequenced derived from the carboxypeptidase analysis (46). As shown in FIG. 13, the entire invertase gene encodes for 532 amino acid residues. The molecular weight of presecretory invertase is 60,649. This enzyme contains 14 potential glycosylation sites although only 9 glycosylation sites have been reported (46, 47).

Figure 15:
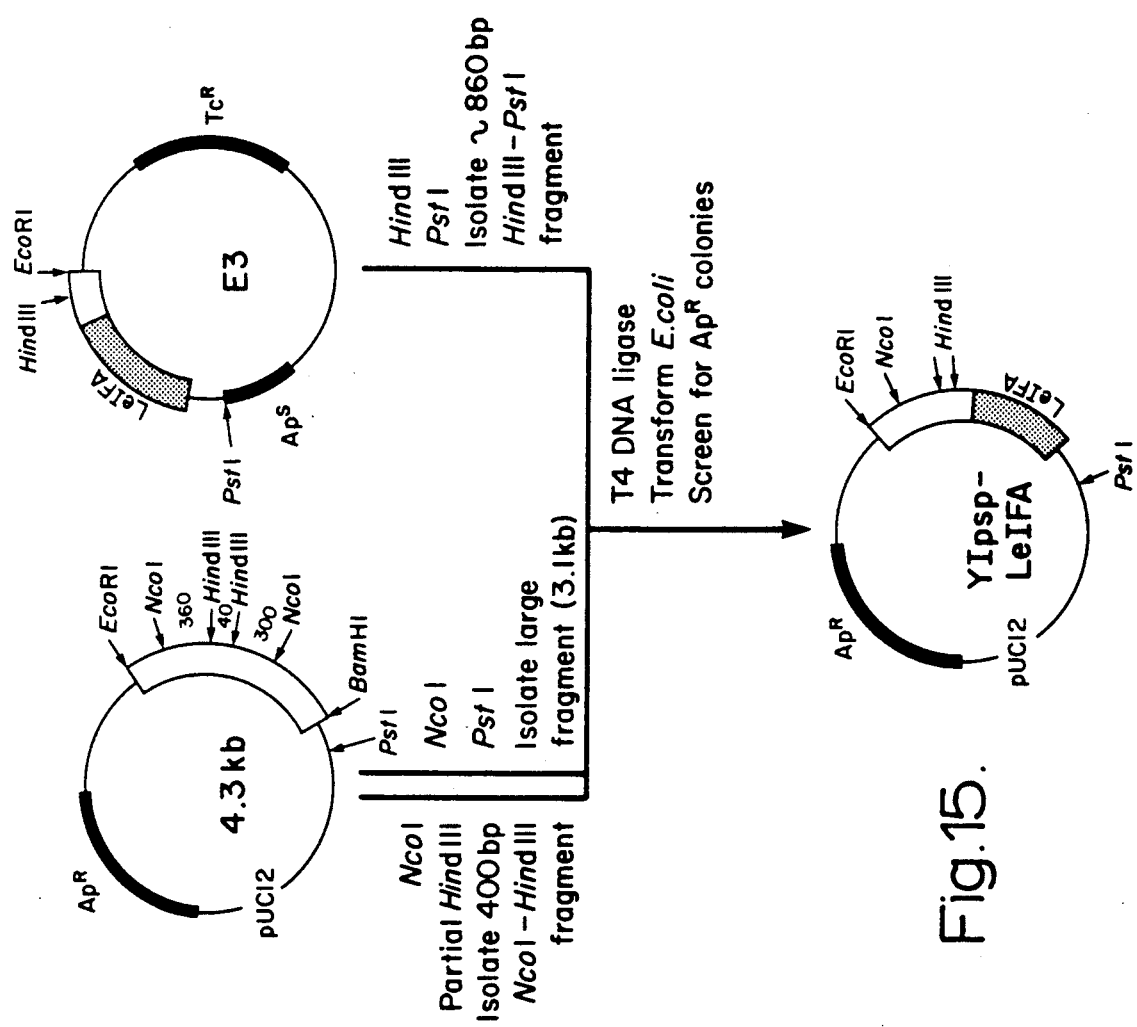
FIG. 15 illustrates the scheme for construction of the invertase promoter and signal codons to the human interferon (LeIFA) gene (YIpsp-LeIFA).

Cloning and Expression of Human Interferon (LeIFA) Gene Using Both the Invertase Promoter and Signal Codons A 1.7 kb fragment from EcoRI to BamHI containing the invertase promoter and front portion of the invertase gene (see FIG. 12) was isolated from clone FI4 and subcloned in a plasmid pUC12 (2.6 kb) as shown in FIG. 15. Plasmid DNA was prepared from the transformant by the method of Birnboim and Doly (20). This plasmid DNA was digested with both NcoI and PstI and the large frament (3.1 kb) was isolated as a vector. The same plasmid DNA was also cut with NcoI and partially cut with HindIII, and the 400 basepair fragment containing the front portion of the invertase signal codons was obtained from the 5 percent polyacrylamide gel. The LeIFA gene was isolated from plasmid DNA of clone E3 described above, which was cut with both HindIII and PstI. This ~860 bp HindIII PstI fragment contains the rear portion of the invertase signal codons and LeIFA gene. Ligation of these three DNA fragments resulted in a plasmid designated as YIpsp-LeIFA which has the invertase promoter (YIp) and signal codons (sp) plus the gene of LeIFA. This 1.8 kb EcoRI-PstI fragment was excised and recloned in the pBR322 by ligation with EcoRI-PstI large fragment of pBR322 (see FIG. 16).

Figure 16:
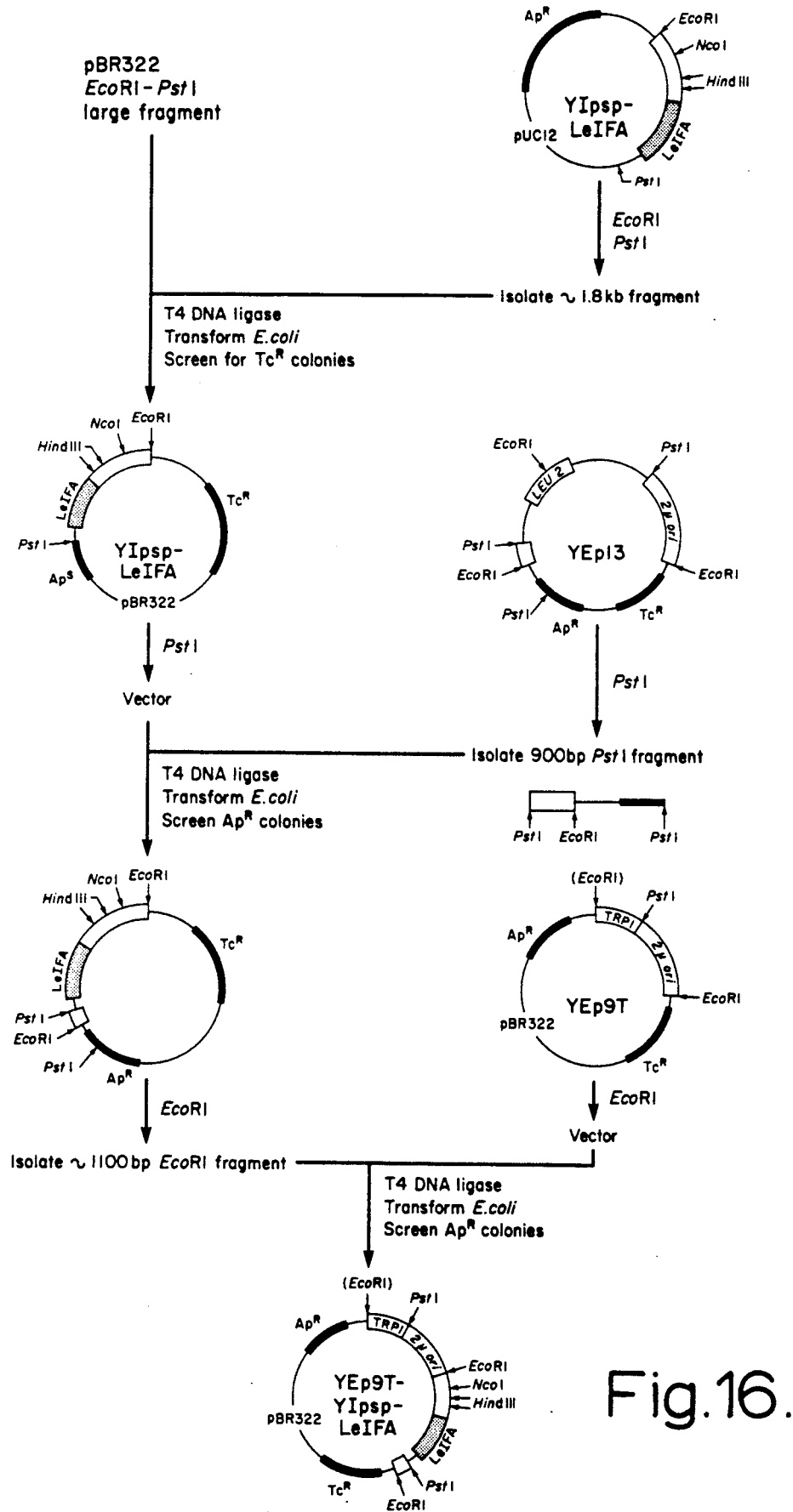
FIG. 16 illustrates the scheme for conversion of YIpsp-LeIFA into an EcoRI fragment for insertion into a yeast plasmid YEp9T (YEp9T-YIpsp-LeIFA).

Plasmid DNA from pBR322 containing YIpsp-LeIFA was linearized with PstI (see FIG. 16). This PstI site was converted into an EcoRI site by inserting a 900 bp PstI fragment isolated from a yeast plasmid YEp13 (37). This 900 bp PstI fragment contains a 654 bp of EcoRI to PstI from pBR322 and a 247 bp of PstI to EcoRI from yeast 2μ plasmid. Thus, insertion of this PstI fragment resulted in the restoration of ampicillin resistance in plasmid-harboring bacteria. The plasmid DNA from ampicillin-resistant transformants was cut with EcoRI, and the ~2.1 kb fragment was isolated and inserted into the sole EcoRI site of the yeast multicopy plasmid YEp9T (see FIG. 16), which possesses a Trpl marker for selection in yeast and a 2μ origin for replicating in yeast. The resulting plasmid designated as YEp9T-YIpsp-LeIFA was used to transform a yeast strain pep4.

Figure 17:
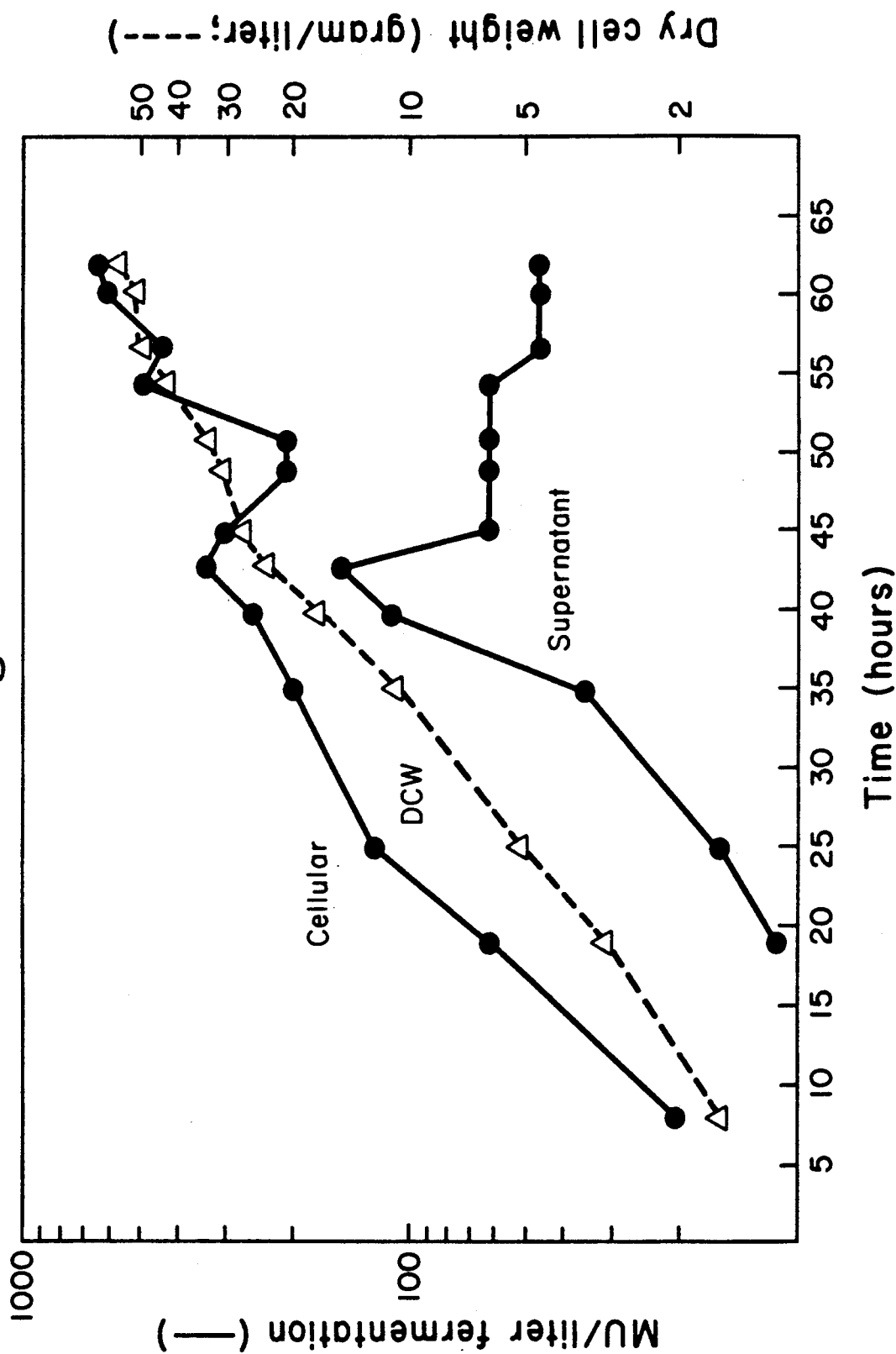
FIG. 17 is a graph of the expression and secretion of LeIFA in yeast using the yeast invertase promoter and its signal coding sequence.

The yeast transformant was grown in fermentation with slow feeding of glucose in the medium. The activity of interferon in the medium reaches 150 million units per liter at 24 g dried cell weight per liter whereas the intracellular interferon is about 350 million units per liter (see FIG. 17). Production of interferon at this stage slowed down, which might be due to injection of more glucose into the medium, resulting in repression of the invertase promoter. By using fructose instead of glucose as a carbon source, production of interferon was not interfered with and is about ten times higher than that in the glucose-containing medium. As was observed with cells transformed with a plasmid containing the PGK promoter and synthetic invertase signal, secretion of LeIFA was higher in the cells transformed with YEp9T-YIpsp-LeIFA, than was observed when LeIFA was expressed fused to the natural signal and processing to form mature LeIFA was complete. cl BIBLIOGRAPHY 1. Novick, P., Field, C., and Schekman, *Cell* 21, 205–216 (1980).
2. Blobel, G. and Dobberstein, B. *J. Cell Biol.* 67, 67, 835–851 (1975).
3. Walter, P. and Blobel, G. *J. Cell Biol.* 91, 545–561 (1981).
4. Heyer, D. I. et al. *J. Cell Biol.* 92, 579–583 (1982).
5. Duntz, et al. *Science* 168, 1472 (1970).
6. Woods, et al., *J. Gen. Microbiol.* 51, 115 (1968).
7. Goeddel, et al., *Nature* 287, 411 (1980).
8. Goeddel, et al., *Nature* 290, 20 (1981).
9. Yelverton, et al., *Nucleic Acids Research* 9, 731 (1981).
10. Goeddel, et al., *Nucleic Acids Research* 8, 4057 (1980).
11. Wertzel, *American Scientist* 68, 664 (1980).
12. Wetzel, et al., *Biochemistry* 19, 6096 (1980).
13. Davis, et al., *Proc. Natl. Acad. Sci. (USA)* 78, 5376 (1981).
14. Hitzeman, et al., *Nature* 293, 717 (1981).
15. Kleid, et al., *Science* 214, 1125 (1981).
16. Lawn et al., *Nucleic Acids Res.* 9, 6103 (1981).
17. Weck, et al., *Nucleic Acids Res.* 9, 6153 (1981).
18. Jacobsen, et al., *Eur. J. Biochem.* 45, 623–627 (1974).
19. Madel, et al., *J. Mol. Biol.* 53, 159–162 (1970).
20. Birnboim, H. C., and Doly, J., *Nucleic Acids Res.* 7, 1513–1523 (1979).
21. Hinnen, A., Hicks, J. B., and Fink, F. R., *Nucleic Acids Res.* 7, 1513–1523 (1979).
21. Hinne, A., Hicks, J. B., and Fink, F. R., *Proc. Natl. Acad. Sci. USA* 75, 1929–1933 (1978).
22. Backman, K., Ptashne, M., and Gilbert, W., *Proc. Natl. Acad. Sci. USA* 73, 4174–4178 (1976).
23. Jones, E. *Genetics* 85, 23 (1976).
24. Maniatis, et al., *Biochemistry* 14, 3787–3794 (1975).
25. Miller, J. H., *Experiments in Molecular Genetics*, pp. 431–433, Cold Spring Harbor Laboratory, Cold Spring Harbor, N.Y.
26. Stewart, W. E., II, *The Interferon System* (Springer, N.Y. 1979).
27. P. Edman, G. Begg, "A Protein Sequencer" *Eur. J. Biochem*, 1, 80–91 (1967).
28. Tarr, G. E. Beecher, J. F., Bell, M and McKean, D. J., *Anal. Biochem.* 75, 621–633 (1976).
29. Wittmann-Liebold, B., Graffunder, H., and Kohls, H., *Anal. Biochem*, 75, 621–633 (1976).
30. Sharp, et al., *Biochemistry* 12, 3055–3063 (1973).
31. Laemmli, *Nature* 227, 680–685 (1970).
32. Smith, *Methods in Enzymology* 65, 499–560 (1980).
33. Messing, et al. *Nucleic Acids Res.* 9, 309–321 1981).
34. Bolivar, et al., *Gene* 2, 95–113 (1977).
35. Hitzeman, et al., *Science*, 219, 620–625 (1983).
36. Towbin, et al., *Proc. Natl. Acad. Sci. USA* 76, 4350 (1979).
37. Broach, et al., *Gene* 8, 121 (1979).
38. Crea, R. and Horn, T. *Nucleic Acids Res.* 8, 2331–2348.
39. Smith, et al., *Methods in Enzymology* 12, 538–541 (1967).
40. Smith, *Methods in Enzymology* 65, 499–560 (1980).
41. Sanger, et al., *Proc. Natl. Acad. Aci. USA* 12, 538–541 (1967).
42. Sanger, Et al., *FEBS Letters* 87, 107–110 (1980).
43. Perlman, et al., *Proc. Natl. Acad. Sci. USA* 79, 781–785 (1982).
44. Carlson, et al., *Cell* 28, 145–154 (1982).

45. Goldstein, et al., *Methods in Enzymology* 42, 504–511 (1975).
46. Trimble, et al., *J. Biol. Chem.* 252, 4409–4412 (1977).
47. Lehle, et al., *J. Biol. Chem.* 254, 12209–12218 (1979).

What is claimed is:

1. A yeast expression vehicle comprising the DNA sequence of a yeast promoter operably linked to a DNA sequence encoding a homologous yeast signal peptide, the final codon of the signal peptide being connected in translation reading frame to a DNA sequence encoding a protein heterologous to the yeast organism, provided that said homologous yeast signal peptide is sufficient, upon expression of a fusion protein containing said signal peptide and heterologous protein, to result in the processing and export of mature heterologous protein into the culture medium of yeast organisms transformed with said vehicle, said heterologous protein being completely processed to the mature form.

2. An expression vehicle according to claim 1 wherein the DNA sequence encoding a signal peptide corresponds to that of the signal peptide for invertase.

3. The expression vehicle of claim 1 wherein the promoter is the invertase promoter.

4. The expression vehicle according to claim 1 wherein the promoter is the yeast 3-phosphoglycerate kinase promoter.

5. The expression vehicle of claim 2 wherein the promoter is the yeast invertase promoter or the yeast 3-phospoglycerate kinase promoter.

6. The expression vehicle of any one of claims 1 to 5 wherein the heterologous protein encoding sequence encodes human leukocyte interferon alpha.

7. A yeast organism transformed by an expression vehicle comprising the DNA sequence of a yeast promoter operably linked to a DNA sequence encoding a homologous yeast signal peptide, the final codon of the signal peptide being connected in translation reading frame to a DNA sequence encoding a protein heterologous to the yeast organism, provided that said homologous yeast signal peptide is sufficient, upon expression of a fusion protein containing said signal peptide and heterologous protein, to result in the processing and export of mature heterologous protein into the culture medium of yeast organisms transformed with said expression vehicle, said heterologous protein being completely processed to the mature form.

8. The yeast organism of claim 7 which is *Saccharomyces cerevisiae*.

9. A yeast cell culture containing a yeast organism transformed by an expression vehicle comprising the DNA sequence of a yeast promoter operably linked to a DNA sequence encoding a homologous yeast signal peptide, the final codon of the signal peptide being connected in translation reading frame to a DNA sequence encoding a protein heterologous to the yeast organism, provided that said homologous yeast signal peptide is sufficient, upon expression of a fusion protein containing said signal peptide and heterologous protein, to result in the processing and export of mature heterologous protein into the culture medium of yeast organisms transformed with said expression vehicle, said heterologous protein being completely processed to the mature form.

10. A process for obtaining a protein heterologous to yeast, which comprises transforming a yeast organism with an expression vehicle comprising the DNA sequence of a yeast promoter operably linked to a DNA sequence encoding a homologous yeast signal peptide, the final codon of the signal peptide being connected in translation reading frame to a DNA sequence encoding a protein heterologous to the yeast organism, provided that said homologous yeast signal peptide is sufficient, upon expression of a fusion protein containing said signal peptide and heterologous protein, to result in the processing and export of mature heterologous protein into the culture medium of yeast organisms transformed with said expression vehicle wherein said heterologous protein is completely processed to the mature form; culturing the transformed organism in a culture medium; and recovering the heterologous protein from the culture medium as completely processed mature heterologous protein.

11. A process for secreting a discrete protein heterologous to yeast into the culture medium, which process comprises transforming a yeast organism with an expression vehicle comprising the DNA sequence of a yeast promoter operably linked to a DNA sequence encoding a homologous yeast signal peptide, the final codon of the signal peptide being connected in translational reading frame to a DNA sequence encoding a protein heterologous to the yeast organism, provided that said homologous yeast signal peptide is sufficient, upon expression of a fusion protein containing said signal peptide and heterologous protein, to result in the processing and export of mature heterologous protein into the culture medium of yeast organisms transformed with said expression vehicle wherein said heterologous protein is completely processed to the mature form and culturing the transformed organism.

* * * * *